United States Patent
Hayakawa et al.

(10) Patent No.: US 10,875,756 B2
(45) Date of Patent: Dec. 29, 2020

(54) INITIAL BACTERIA CONFIRMATION METHOD IN CONTENT FILLING SYSTEM, METHOD FOR VERIFYING CONTENT FILLING SYSTEM, AND CULTURE MEDIUM

(71) Applicant: DAI NIPPON PRINTING CO., LTD., Tokyo-to (JP)

(72) Inventors: Atsushi Hayakawa, Tokyo-to (JP); Yuiko Wada, Tokyo-to (JP); Ryuichi Tamagawa, Tokyo-to (JP); Tsubasa Tokimoto, Tokyo-to (JP)

(73) Assignee: DAI NIPPON PRINTING CO., LTD., Tokyo-to (JP)

( * ) Notice: Subject to any disclaimer, the term of this patent is extended or adjusted under 35 U.S.C. 154(b) by 126 days.

(21) Appl. No.: 16/083,664

(22) PCT Filed: Mar. 7, 2017

(86) PCT No.: PCT/JP2017/009091
§ 371 (c)(1),
(2) Date: Sep. 10, 2018

(87) PCT Pub. No.: WO2017/154933
PCT Pub. Date: Sep. 14, 2017

(65) Prior Publication Data
US 2019/0071297 A1  Mar. 7, 2019

(30) Foreign Application Priority Data

Mar. 8, 2016 (JP) ................. 2016-044655
Apr. 8, 2016 (JP) ................. 2016-078260

(51) Int. Cl.
*B67C 7/00* (2006.01)
*C12Q 1/22* (2006.01)
(Continued)

(52) U.S. Cl.
CPC ............ *B67C 7/0073* (2013.01); *B65B 55/02* (2013.01); *B65B 55/04* (2013.01); *B65B 55/10* (2013.01);
(Continued)

(58) Field of Classification Search
CPC ... B67C 7/0073; B67C 3/02; B67C 2007/006; B65B 55/02; B65B 55/04
(Continued)

(56) References Cited

U.S. PATENT DOCUMENTS 4,992,247 A * 2/1991 Foti .......................... A61L 2/20
422/28
5,016,688 A * 5/1991 Suzuki ................... C12M 23/48
141/129
(Continued)

FOREIGN PATENT DOCUMENTS

| CN | 101018711 A | 8/2007 |
| CN | 102112374 A | 6/2011 |

(Continued)

OTHER PUBLICATIONS

Sep. 20, 2018 International Preliminary Report on Patentability issued in International Patent Application No. PCT/JP2017/009091.
(Continued)

*Primary Examiner* — Gloria R Weeks
(74) *Attorney, Agent, or Firm* — Oliff PLC

(57) ABSTRACT

A bottle is conveyed to a filling device without being sterilized by a container sterilizer, and a culture medium is filled inside the bottle by using the filling device. Then, the bottle is capped with a cap using a cap attachment device. Thereafter, whether or not bacteria survive or propagate in the culture medium in the bottle is verified.

9 Claims, 8 Drawing Sheets

(51) Int. Cl.
*B65B 55/02* (2006.01)
*B67C 3/00* (2006.01)
*B65B 55/04* (2006.01)
*B65B 55/10* (2006.01)

(52) U.S. Cl.
CPC .............. *B67C 3/00* (2013.01); *B67C 7/004* (2013.01); *C12Q 1/22* (2013.01); *B67C 2007/006* (2013.01); *B67C 2007/0066* (2013.01)

(58) Field of Classification Search
USPC .................... 53/426, 425, 111 RC, 266.1
See application file for complete search history.

(56) References Cited

U.S. PATENT DOCUMENTS

| | | | | |
|---|---|---|---|---|
| 5,054,265 A * | 10/1991 | Perigo | .................... | B21D 51/32 53/425 |
| 5,720,148 A * | 2/1998 | Bedin | .................... | B65B 55/02 53/127 |
| 5,953,884 A * | 9/1999 | Lawecki | ................. | B65B 3/006 53/428 |
| 7,600,542 B2 * | 10/2009 | Wiedemann | ............ | A23L 3/001 141/85 |
| 7,685,794 B2 * | 3/2010 | Nagatani | ............... | B65B 55/025 53/111 R |
| 8,181,429 B2 * | 5/2012 | Iwashita | ................. | B65B 55/10 53/426 |
| 8,869,496 B2 * | 10/2014 | Laumer | ................. | B67C 7/0073 53/173 |
| 2006/0086065 A1 * | 4/2006 | Tomalesky | ............ | B65B 7/2835 53/425 |
| 2007/0101681 A1 * | 5/2007 | Iwashita | ................. | B65B 55/14 53/425 |
| 2009/0007522 A1 * | 1/2009 | Sakai | ...................... | A23F 3/163 53/426 |
| 2009/0293429 A1 * | 12/2009 | Till | ........................... | A61L 2/08 53/425 |
| 2010/0037984 A1 * | 2/2010 | Hiroya | ................. | B67C 7/0073 141/59 |
| 2011/0005958 A1 * | 1/2011 | Stepovich | .............. | G05D 21/02 206/524.1 |
| 2013/0071527 A1 | 3/2013 | Pesce et al. | | |
| 2014/0109529 A1 * | 4/2014 | Hayakawa | ............. | B67C 3/242 53/558 |
| 2014/0234950 A1 * | 8/2014 | Wolters | ................. | C12M 23/08 435/287.9 |
| 2014/0377443 A1 * | 12/2014 | Tanzosh | .................... | A23L 3/22 426/599 |
| 2016/0002018 A1 * | 1/2016 | Clusserath | ............. | B29C 49/66 53/426 |
| 2016/0137473 A1 * | 5/2016 | Guamis Alegre | ..... | B67C 7/0073 53/426 |
| 2016/0199257 A1 * | 7/2016 | Husnu | .................... | B65B 3/003 206/570 |

FOREIGN PATENT DOCUMENTS

| | | |
|---|---|---|
| EP | 1384670 A1 | 1/2004 |
| EP | 1790571 A1 | 5/2007 |
| JP | H02-242722 A | 9/1990 |
| JP | H04-17511 A | 1/1992 |
| JP | H06-181737 A | 7/1994 |
| JP | H07-008296 A | 1/1995 |
| JP | H08-140697 A | 6/1996 |
| JP | H10-152116 A | 6/1998 |
| JP | 2003-181404 A | 7/2003 |
| JP | 2004-121168 A | 4/2004 |
| JP | 2004-201668 A | 7/2004 |
| JP | 2006-238838 A | 9/2006 |
| JP | 2008-131896 A | 6/2008 |
| JP | 2009-280222 A | 12/2009 |
| JP | 2010-036973 A | 2/2010 |
| JP | 2012-030879 A | 2/2012 |
| WO | 2010-016539 A1 | 2/2010 |
| WO | 2016-047607 A1 | 3/2016 |

OTHER PUBLICATIONS

Aug. 13, 2019 Search Report issued in European Patent Application No. 17763273.4.
Mar. 19, 2019 Office Action issued in Japanese Patent Application No. 2017-127901.
May 23, 2017 International Search Report issued in International Patent Application No. PCT/JP2017/009091.
May 23, 2017 Written Opinion issued in International Patent Application No. PCT/JP2017/009091.
Feb. 24, 2017 Office Action issued in Japanese Patent Application No. 2016-044655.
Mar. 24, 2017 Office Action issued in Japanese Patent Application No. 2016-078260.
Mar. 20, 2018 Office Action issued in Japanese Patent Application No. 2017-127877.
Apr. 27, 2018 Office Action issued in Japanese Patent Application No. 2017-127888.
May 25, 2018 Office Action issued in Japanese Patent Application No. 2017-127893.
Jun. 8, 2018 Office Action issued in Japanese Patent Application No. 2017-127899.
Jun. 8, 2018 Office Action issued in Japanese Patent Application No. 2017-127901.
May 25, 2018 Office Action issued in Japanese Patent Application No. 2017-127895.
Oct. 23, 2018 Office Action issued in Japanese Patent Application No. 2017-127901.
Mar. 12, 2020 Office Action issued in European Patent Application No. 17763273.4.
Liu Qianhong et al; "Comparative transcriptome analysis of Brucella melitensisin an acidic environment: Identification of the two-component response regulator involved in the acid resistance and virulence of Brucella"; Microbial Pathogenesis, Academic Press Limited; New York, NY; vol. 91; Dec. 2015; pp. 92-98.
May 15, 2020 Office Action issued in Japanese Patent Application No. 2019-111108.
Jun. 2, 2020 Office Action issued in Chinese Patent Application No. 201780015334.8.
Sep. 4, 2020 Office Action issued in European Patent Application No. 17 763 273.4.
Oct. 6, 2020 Office Action issued in Japanese Patent Application No. 2019-111108.

* cited by examiner

INITIAL BACTERIA CONFIRMATION METHOD IN CONTENT FILLING SYSTEM, METHOD FOR VERIFYING CONTENT FILLING SYSTEM, AND CULTURE MEDIUM

TECHNICAL FIELD

The present invention relates to an initial bacteria confirmation method in a content filling system, a method for verifying a content filling system, and a culture medium used for such a verification method.

BACKGROUND ART

A sterile filling system (aseptic filling system) has been known in which a sterilized content is filled inside a sterilized container (PET bottle) in a sterile environment and then the container is capped with a cap. Specifically, in the sterile filling system, a molded container is fed to the sterile filling system, and a hydrogen peroxide aqueous solution as a disinfectant is sprayed into the container in the sterile filling system. After that, the container is dried and sterilized, and then, a content is aseptically filled inside the container. As another method, there is a method of adding dropwise a small amount of disinfectant on an inner surface of a container at the time of molding the container, sealing a mouth to sterilize the inner surface of the container with vapor of the vaporized disinfectant (hydrogen peroxide), feeding the sterilized container to a sterile filling system, sterilizing an outer surface of the container in the sterile filling system, and then opening the mouth to aseptically fill the content.

For example, it is necessary to confirm whether or not the sterility of the system is ensured before actual filling of the container is started at an initial stage of the sterile filling system. For this reason, various tests are being conducted to confirm the sterility of the system. In order to comprehensively evaluate the sterility of the sterile filling system at a final stage after such various tests, an evaluation method using a container filled with a culture medium has been performed.

For example, Patent Literature 1 discloses a method of verifying the sterilization level of a container by filling the container with a sterilized treatment culture medium.

However, in the sterile filling system, it is conceivable that containers and caps are contaminated from the beginning. In such a case, even if a content is aseptically filled inside the container using the sterile filling system, there is a fear that bacteria may propagate inside the finished beverage product, and thus, measures such as increasing the amount of disinfectant are required. Accordingly, it is important to accurately grasp beforehand a degree of bacterial contamination of containers and caps, that is, the initial number of bacteria in the containers and the caps (the number of bacteria adhering to the containers and the caps before filling).

Generally, in a test using such a culture medium, a neutral medium (pH=6 or more and 8 or less) is used as a culture medium since almost all the bacteria can be detected. By using the neutral medium, it is possible to deal with whatever kind of content is filled in the sterile filling system. In practice, however, the content to be filled in the sterile filling system may be limited to certain kinds. In this case, performing a test for detecting all the bacteria unnecessarily strains the system, resulting in an increase in the cost of facilities, medicines, energy and the like.

CITATION LIST

Patent Literature

Patent Literature 1: JP 2010-36973 A

The present invention has been made in consideration of such points and an object of the invention is to provide an initial bacteria confirmation method in which in a content filling system, initial bacteria adhering to containers and caps can be accurately grasped using actual manufacturing equipment. Another object of the invention is to provide a method for verifying a content filling system, in which costs required for facilities, medicines, energy and the like can be suppressed by using a suitable culture medium matched to a content to be filled in the content filling system, and a culture medium.

SUMMARY OF INVENTION

The present invention is an initial bacteria confirmation method for confirming initial bacteria in a container with the use of a content filling system having a container sterilizer which sterilizes the container, a filler which fills a content in the container, and a cap attachment device which caps the container with a cap, and the initial bacteria confirmation method includes a step of conveying the container to the filler without sterilizing the container by the container sterilizer, a step of filling a culture medium in the container with the use of the filler, a step of capping the container with the cap using the cap attachment device, and a step of verifying whether or not the bacteria survive or propagate in the culture medium in the container.

The present invention is an initial bacteria confirmation method further including a step of adjusting sterilization conditions in the container sterilizer based on results of the verification.

The present invention is an initial bacteria confirmation method for confirming initial bacteria in a cap with the use of a content filling system having a filler which fills a content in a container, a cap sterilizer which sterilizes the cap, and a cap attachment device which caps the container with the cap, and the initial bacteria confirmation method includes a step of filling a culture medium in the container with the use of the filler, a step of conveying the cap to the cap attachment device without sterilizing the cap by the cap sterilizer, a step of capping the container with the cap using the cap attachment device, and a step of verifying whether or not the bacteria survive or propagate in the culture medium in the container.

The present invention is an initial bacteria confirmation method further including a step of adjusting sterilization conditions in the cap sterilizer based on results of the verification.

In the initial bacteria confirmation method of the present invention, the content is acidic, and pH of the culture medium is 3.5 or more and 4.6 or less.

In the initial bacteria confirmation method of the present invention, the content is neutral, and pH of the culture medium is 6 or more and 8 or less.

In the initial bacteria confirmation method of the present invention, in the verifying step, a physical movement is added to the culture medium in the container.

According to the present invention, it is possible to grasp initial bacteria adhering to the container and the cap.

The present invention is a method for verifying a content filling system using a culture medium and the method includes a step of feeding a container to the content filling system, a step of filling a culture medium in the container in the content filling system and then capping the container, and a step of verifying whether or not the bacteria survive or propagate in the culture medium in the container, and in this verification method, characteristics of the culture medium are matched to characteristics of the content to be filled in the content filling system, the characteristics influencing propagation of the bacteria.

In the verification method of the present invention, the characteristic of the content is pH of the content, and pH of the culture medium is adjusted to the pH of the content.

In the verification method of the present invention, the pH of the culture medium is 3.5 or more and 4.6 or less.

In the verification method of the present invention, the content contains carbonic acid gas, and the carbonic acid gas is dissolved in the culture medium.

In the verification method of the present invention, the content does not contain at least one of a carbon source and a nitrogen source, and at least one of the carbon source and the nitrogen source is not allowed to contain in the culture medium.

In the verification method of the present invention, the content does not contain at least one of a carbon source and a nitrogen source, and catechin is dissolved in the culture medium.

In the verification method of the present invention, the characteristic of the content is the total organic carbon content, and the total organic carbon content of the culture medium is adjusted to the total organic carbon content of the content.

In the verification method of the present invention, the content contains catechin, and the catechin is dissolved in the culture medium.

The present invention is a culture medium used for the verification method, and in this culture medium, characteristics of the culture medium are matched to the characteristics of the content to be filled in the content filling system, the characteristics influencing propagation of the bacteria.

According to the present invention, the characteristics of the culture medium are matched to the characteristics of the content to be filled in the content filling system, whereby it is possible to verify whether or not bacteria propagate in the culture medium in the container while suppressing costs required for facilities, medicines, energy and the like.

DESCRIPTION OF EMBODIMENTS

First Embodiment

Figure 1:
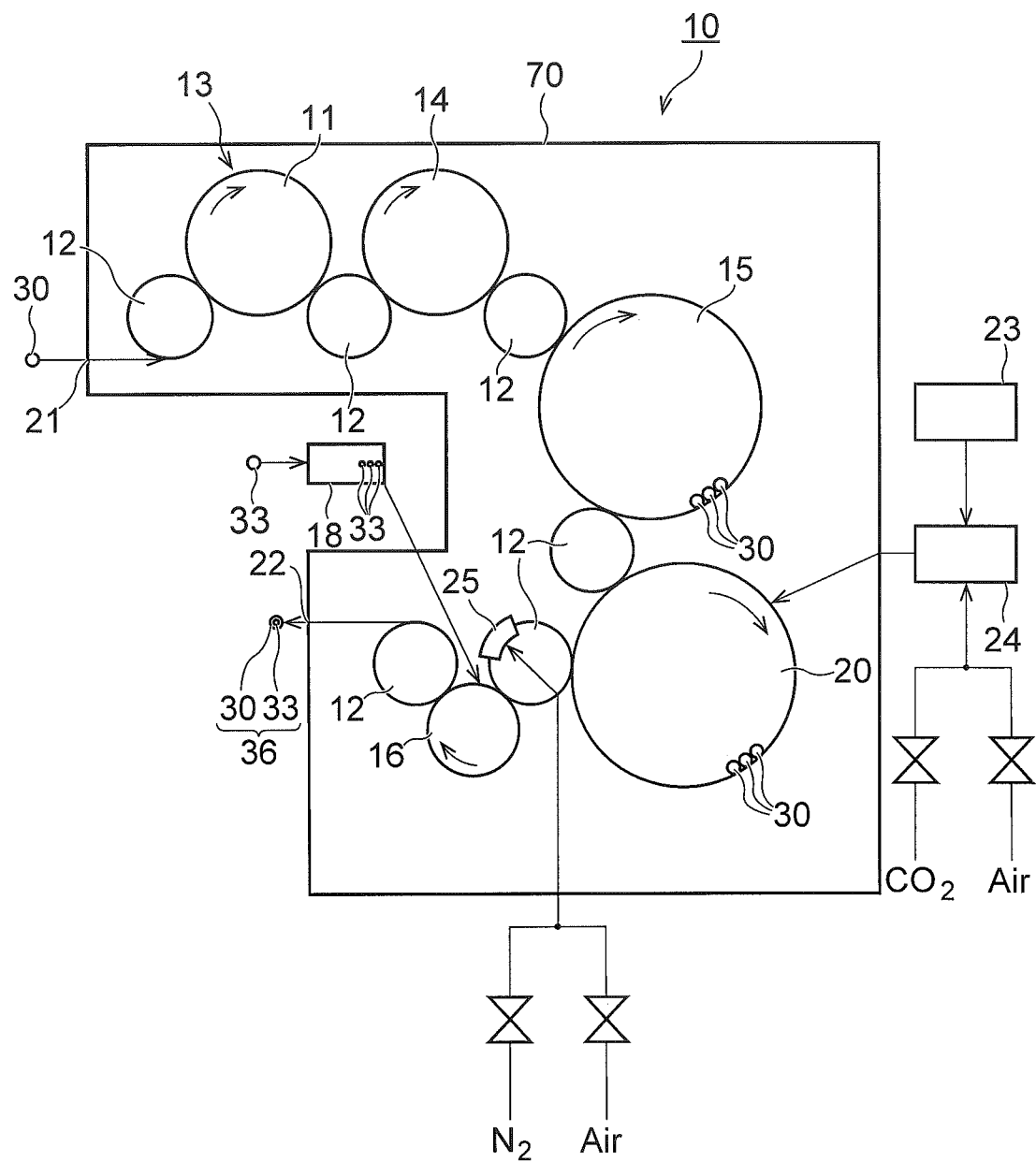
FIG. 1 is a schematic plan view illustrating a content filling system used in an initial bacteria confirmation method according to a first embodiment of the present invention.
Figure 2:
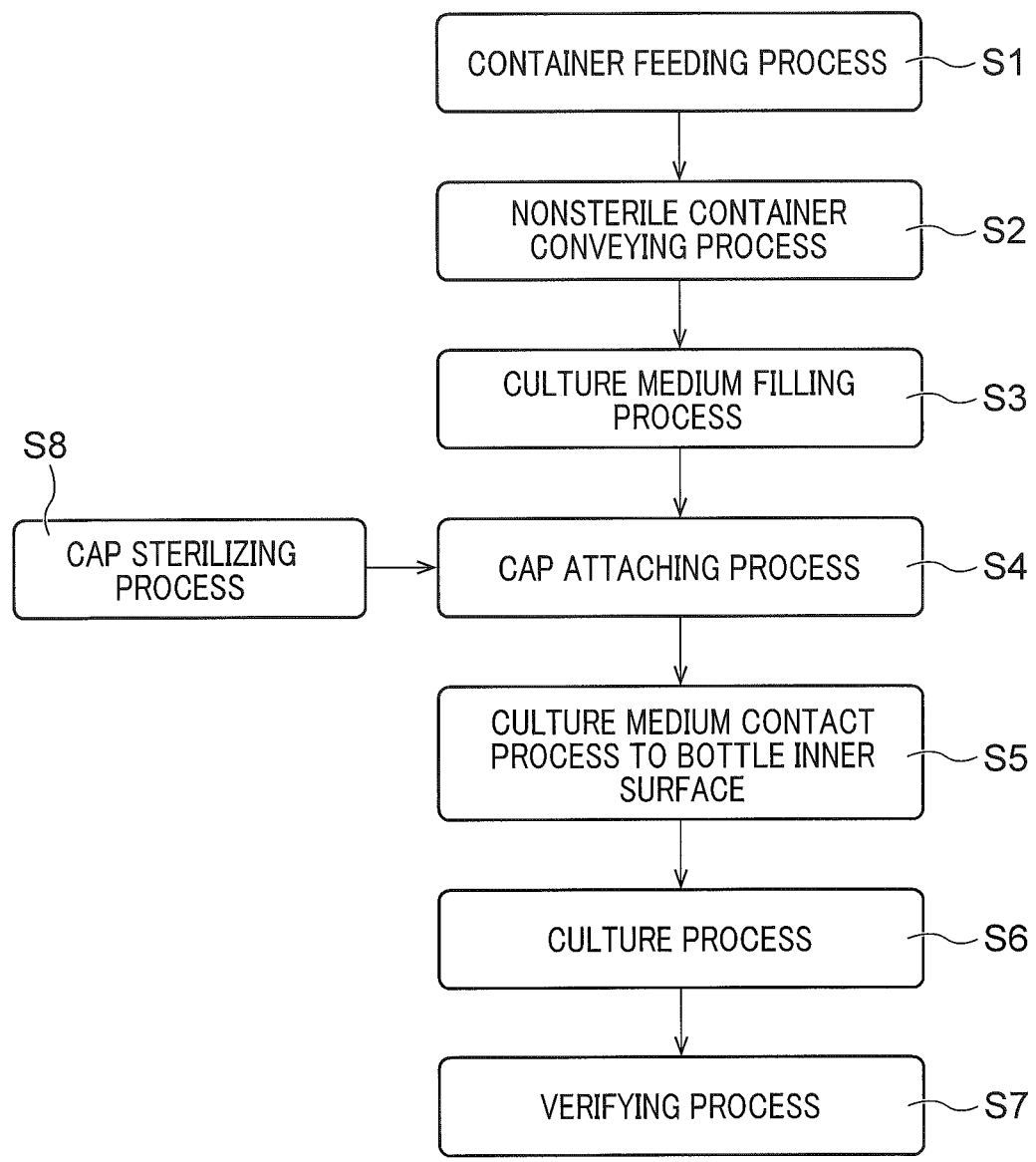
FIG. 2 is a flowchart showing an initial bacteria confirmation method according to the first embodiment of the present invention.
Figure 3:
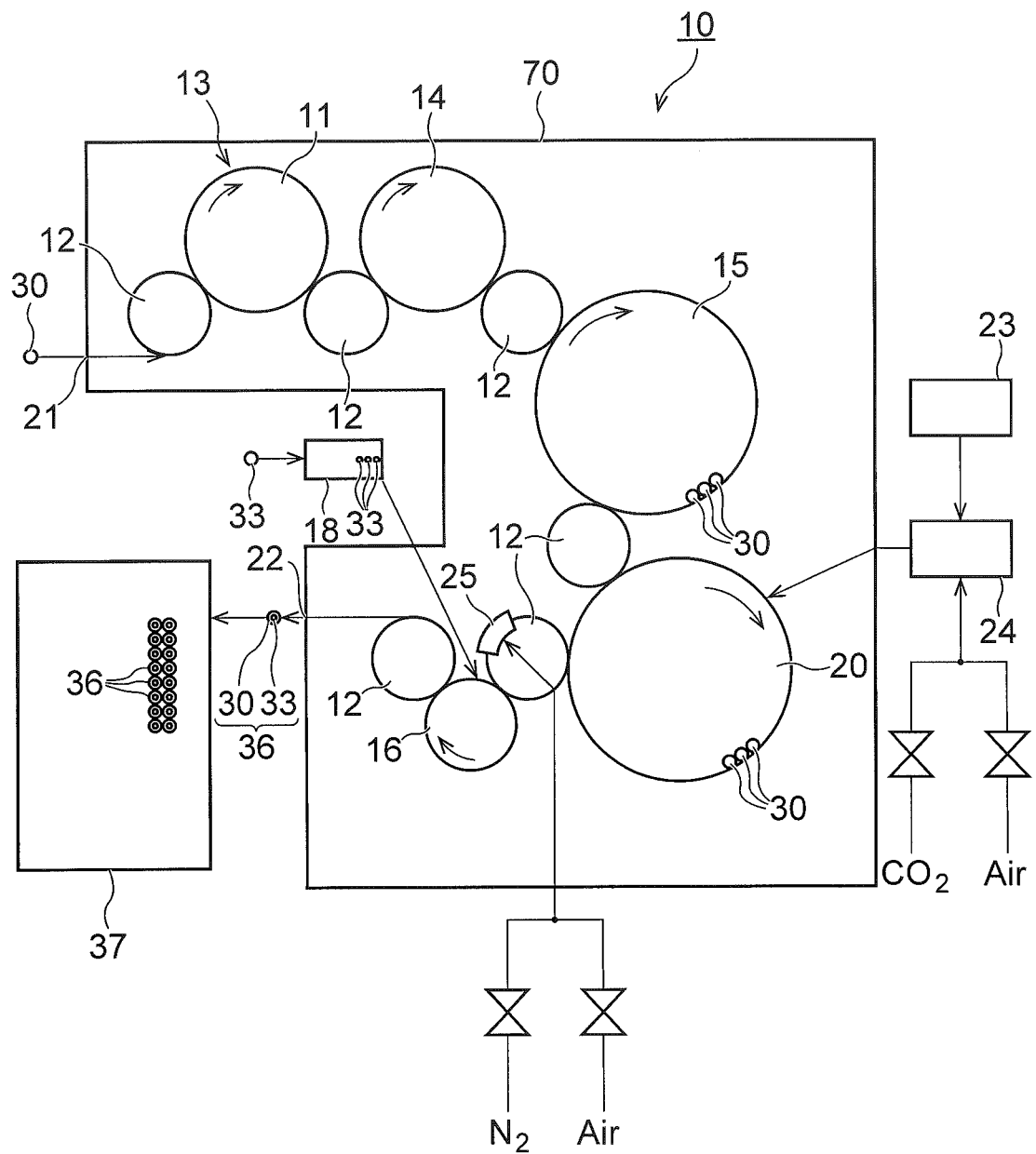
FIG. 3 is a schematic plan view illustrating the content filling system when the initial bacteria confirmation method is executed according to the first embodiment of the present invention.

A first embodiment of the present invention will be described below with reference to the drawings. FIGS. 1 to 3 illustrate the first embodiment of the present invention.

(Content Filling System)

First, a content filling system (sterile filling system, aseptic filling system) according to the present embodiment will be described with reference to FIG. 1.

A content filling system 10 illustrated in FIG. 1 is a system for filling a bottle (container) 30 with a content such as a beverage. The bottle 30 can be made by performing biaxial stretching blow molding on a preform made by performing injection molding on a synthetic resin material. A material of the bottle 30 to be used is preferably a thermoplastic resin such as polyethylene (PE), polypropylene (PP), polyethylene-terephthalate (PET), or polyethylene naphthalate (PEN). In addition, the container may be glass, a can, paper, a pouch, or a composite container of these. The present embodiment will describe an example of a case where a bottle is used for the container.

As illustrated in FIG. 1, the content filling system 10 includes a bottle feeding portion 21, a sterilizer 11, an air rinse device 14, a sterile water rinse device 15, a filling device (filler) 20, a cap attachment device (a capper, a seamer, and a capping machine) 16, and a product bottle conveyor 22. These bottle feeding portion 21, sterilizer 11, air rinse device 14, sterile water rinse device 15, filling device 20, cap attachment device 16, and product bottle conveyor 22 are disposed in this order along a conveying direction thereof from an upstream side to a downstream side. Between the sterilizer 11, the air rinse device 14, the sterile water rinse device 15, the filling device 20, and the cap attachment device 16, a plurality of convey wheels 12 for conveying the bottle 30 between these devices is provided.

The bottle feeding portion 21 successively receives the empty bottle 30 from an outside to the content filling system 10, and conveys the received bottle 30 to the sterilizer 11.

A bottle molding portion (not shown) which molds the bottle 30 by performing biaxial stretching blow molding on a preform may be provided on the upstream side of the bottle feeding portion 21. In such a case, the process starting upon feeding of the preform, and then molding of the bottle 30, and ending upon filling of the bottle 30 with the content and capping may be performed continuously. In this case, instead of the bottle 30 having a large volume, a preform having a small volume can be carried from the outside to the content filling system 10, so that the shipping cost can be reduced.

The sterilizer 11 sterilizes the interior of the bottle 30 by injecting a disinfectant into the bottle 30. This allows the bottle 30 to be sterilized by the disinfectant prior to filling the content, so that although survival of bacterial spores is allowed, survival of vegetative cells of bacteria, mold and yeast is not allowed. As the disinfectant, a hydrogen peroxide aqueous solution is used, for example. In the sterilizer 11, mist or gas of the hydrogen peroxide aqueous solution is generated, and the mist or gas is sprayed on an inner and outer surfaces of the bottle 30. Since the inside of the bottle 30 is thus sterilized by the mist or gas of the hydrogen peroxide aqueous solution, the inner surface of the bottle 30 is sterilized uniformly.

The air rinse device 14 supplies sterile heated air or room temperature air into the bottle 30 to remove foreign matter, hydrogen peroxide, and the like from the inside of the bottle 30 while activating the hydrogen peroxide.

The sterile water rinse device 15 washes the bottle 30, sterilized by hydrogen peroxide as a disinfectant, with sterilized water at 15° C. to 85° C. As a result, hydrogen peroxide adhering to the bottle 30 is washed off, and foreign matter is removed. The sterile water rinse device 15 is not necessarily provided.

In the present embodiment, the container sterilizer 13 is constituted by the above-described sterilizer 11.

The filling device 20 fills the previously sterilized content from a mouth of the bottle 30 into the bottle 30. This filling device 20 fills the content in the empty bottle 30. In the filling device 20, while a plurality of the bottles 30 is rotated (revolved), the content is filled inside the bottles 30. This content may be filled inside the bottle 30 at room temperature. The content is previously sterilized by heating or the like, cooled to room temperature of 3° C. or more and 40° C. or less, and then filled inside the bottle 30. As described above, survival of bacterial spores is allowed in the bottle 30. For this reason, there is no need to fill the bottle 30 with the content heated to a high temperature as in the prior art, to hold a state in which the bottle 30 is filled with the content for a long time, or to heat a product bottle 35 (to be described later), obtained by closing the bottle 30 filled with the content with the cap 33, from outside and sterilize the content.

The content filled from the filling device 20 has predetermined characteristics which influence propagation of bacteria. In the present embodiment, the predetermined characteristics may be pH of the content. More specifically, the content may be an acid beverage. The acidity of the beverage is preferably less than pH 4.6, more preferably less than pH 4.0. Examples of beverages having pH of 4.0 or more and pH of 4.6 or less include tomato juice and vegetable juice, and examples of beverages having pH of less than 4.0 include lemon tea, orange juice, lactic carbonate drink, functional drink, carbonate lemon juice, grape juice, and fruit juice.

In general, bacterial spores maintain a bacteriostatic state without germinating in a liquid having relatively high degree of acidity (for example, a liquid having pH of less than 4.6, preferably less than 4.0), and thus the content is preserved without being corrupted. Accordingly, as described above, although the bacterial spores remain alive inside the bottle 30 to be filled by the filling device 20, a sterilized content having acidity (for example, pH of less than 4.6, preferably less than 4.0) capable of preventing growing of bacterial spores is filled inside the bottle 30, whereby the beverage can be prevented from being denatured and becoming corrupted.

The cap attachment device 16 caps the bottle 30 by attaching the cap 33 to the mouth of the bottle 30. In the cap attachment device 16, the mouth of the bottle 30 is capped with the cap 33 and then sealed so as to prevent external air or virus from invading into the bottle 30. In the cap attachment device 16, while the plurality of bottles 30 filled with the content rotates (revolves), the caps 33 are attached to the mouths of the bottles 30. Thus, by attaching the cap 33 to the mouth of the bottle 30, it is possible to obtain the product bottle 35.

The cap 33 is previously sterilized by the cap sterilizer 18. The cap sterilizer 18 is disposed inside a sterile chamber 70 (to be described later) and near the cap attachment device 16, for example. In the cap sterilizer 18, a large number of the caps 33 carried in from the outside of the content filling system 10 are preliminarily collected and then conveyed in a row toward the cap attachment device 16. Mist or gas of hydrogen peroxide is blown against an inner and outer surfaces of the cap 33 on the way of conveyance of the cap 33 toward the cap attachment device 16 and then dried with hot air and sterilized.

The product bottle conveyor 22 continuously conveys the product bottle 35 with the cap 33 attached by the cap attachment device 16 to the outside of the content filling system 10.

In addition, the content filling system 10 includes the sterile chamber 70. The sterile chamber 70 houses the sterilizer 11, the air rinse device 14, the sterile water rinse device 15, the filling device 20, the cap sterilizer 18, and the cap attachment device 16, which have been described above. This content filling system 10 may be, for example, a sterile filling system. In this case, the interior of the sterile chamber 70 is kept in a sterile state.

Alternatively, the content filling system 10 may be a high temperature filling system that fills a content at a high temperature of 85° C. or more and less than 100° C. The content filling system 10 may also be a medium temperature filling system that fills a content at a medium temperature of 55° C. or more and less than 85° C. On the other hand, the technical idea according to the present embodiment can also be applied to sterile packaging using post-sterilization such as retort sterilization.

(Content Filling Method)

Next, a content filling method using the above-described content filling system 10 (FIG. 1) will be described. In the following description, a filling method at a normal time, that is, a content filling method in which a content such as a beverage is actually filled inside the bottle 30 to produce the product bottle 35 will be described.

First, the plurality of empty bottles 30 is sequentially fed from the outside of the content filling system 10 to the bottle feeding portion 21. The bottle 30 is sent from the bottle feeding portion 21 to the sterilizer 11 by the convey wheel 12 (container feeding process).

Then, in the sterilizer 11 constituting the container sterilizer 13, the bottle 30 is sterilized using a hydrogen peroxide aqueous solution as a disinfectant (sterilization process). At this time, the hydrogen peroxide aqueous solution is gas or mist vaporized once at a temperature not less than the boiling point, and is supplied toward the bottle 30. The mist of the hydrogen peroxide aqueous solution adheres to the entire inner surface of the bottle 30 and sterilizes vegetative cells of bacteria, mold and yeast in the bottle 30. The amount of mist of hydrogen peroxide to be supplied into the bottle 30 is, for example, 5 μL/bottle or more and 50 μL/bottle or less, and in the case of hydrogen peroxide gas, the amount is 1 mg/L or more and 5 mg/L or less. Although the sterilizing force of the hydrogen peroxide is determined as an extent such that the vegetative cells of bacteria, mold and yeast can be sterilized, but bacterial spores cannot be sterilized. Accordingly, the amount of the hydrogen peroxide to be used can be reduced.

Subsequently, the bottle 30 is sent to the air rinse device 14 by the convey wheel 12, and sterile heated air or room temperature air is supplied in the air rinse device 14, whereby foreign matter, hydrogen peroxide, and the like are removed from the bottle 30 while hydrogen peroxide is activated. Subsequently, the bottle 30 is conveyed to the sterile water rinse device 15 by the convey wheel 12. In the sterile water rinse device 15, washing with sterile water at 15° C. to 85° C. is performed (rinsing process). Specifically, sterile water at 15° C. to 85° C. is supplied into the bottle 30 at a flow rate of 5 L/min or more and 15 L/min or less. At this time, it is preferable that the bottle 30 takes an inverted attitude, and the sterile water is supplied into the bottle 30 through the downwardly opened mouth, and flows out of the bottle 30 from the mouth. With this hot water, hydrogen peroxide adhering to the bottle 30 is washed off, and foreign matter is removed.

Subsequently, the bottle 30 is conveyed to the filling device 20 by the convey wheel 12. In the filling device 20, while the bottle 30 is rotated (revolved), the content is filled inside the bottle 30 from the mouth (filling process).

The content is previously prepared before filled inside the bottle 30 by the filling device 20, and heating sterilization treatment is performed. As described above, the content may have a predetermined pH as a characteristic influencing propagation of bacteria. Specifically, the content may be an acid beverage preferably having pH of less than 4.6, more preferably pH of less than 4. In general, the heating temperature is about 60° C. or more and 120° C. or less when the acidity of the content is less than pH 4.0, and the heating temperature is about 115° C. or more and 150° C. or less when the acidity of the content is pH 4.0 or more. As a result, virus which may be grown in the product bottle 35 in the content before the filling thereof can be completely sterilized. The content after the heating sterilization treatment is cooled to the room temperature of about 3° C. or more and 40° C. or less.

In the filling device 20, the content sterilized and cooled to the room temperature is filled inside the sterilized bottle 30 at the room temperature. The temperature of the content during filling is, for example, about 3° C. or more and 40° C. or less. As described above, the acidity of the content is preferably less then 4.6, more preferably less than pH 4.0, and specific examples of the content include tomato juice, vegetable juice, lemon tea, orange juice, lactic carbonate drink, functional drink, carbonate lemon juice, grape juice, and fruit juice. That is, according to such a content filling method, the product bottles 35 filled with almost all kinds of beverages and drinks except for barley tea, mixed tea and milked drink having pH of 4.6 or more can be manufactured. It goes without saying that it is also possible to manufacture the product bottle 35 for carbonate drinks such as cola or cider including no animal or vegetable components and having carbon gas pressure of 1.0 kg/cm$^2$ (20° C.) or more.

Subsequently, the bottle 30 filled with the content is conveyed to the cap attachment device 16 by the convey wheel 12.

On the other hand, the cap 33 is previously sterilized by the cap sterilizer 18 (cap sterilization process). During this time, the cap 33 is first carried into the cap sterilizer 18 from the outside of the content filling system 10. Subsequently, the mist or gas of hydrogen peroxide is blown against the cap 33 in the cap sterilizer 18 to sterilize the inner and outer surfaces of the cap 33, and then the cap 33 is dried with hot air and sent to the cap attachment device 16.

Subsequently, in the cap attachment device 16, the sterilized cap 33 is attached to the mouth of the bottle 30 conveyed from the filling device 20, whereby the product bottle 35 is obtained (cap attaching process).

Thereafter, the product bottle 35 is conveyed from the cap attachment device 16 to the product bottle conveyor 22 and is carried toward the outside of the content filling system 10.

The respective processes from the sterilization process to the cap attaching process are performed in a sterile atmosphere surrounded by the sterile chamber 70, that is, in a sterile environment. The interior of the sterile chamber 70 is sterilized by preliminarily spraying hydrogen peroxide, applying hot water or the like so as to allow survival of bacterial spores but not allow survival of vegetative cells of bacteria, mold and yeast. After the sterilization treatment, aseptic air of positive pressure is supplied into the sterile chamber 70 so that the aseptic air is always blown toward the exterior of the sterile chamber 70.

The production (conveying) speed of the bottle 30 in the content filling system 10 is preferably 100 bpm or more and 1500 bpm or less. Here, a convey speed of the bottle 30 per minute is referred to as bottle per minute (bpm).

(Initial Bacteria Confirmation Method in Content Filling System)

Next, an initial bacteria confirmation method for verifying sterility of the bottle 30 with the use of the above-described content filling system 10 (FIG. 1) will be described.

In the initial bacteria confirmation method according to the present embodiment, whether or not the sterility of the bottle 30 filled with the content in the content filling system 10 is ensured is confirmed. This initial bacteria confirmation method may be performed, for example, at an early stage immediately after completion of the content filling system 10, that is, before filling the bottle 30 by actually using the content filling system 10 and starting production of the product bottle 35. Alternatively, the initial bacteria confirmation method according to the present embodiment may be performed when there is a risk of affecting sterility, such as when some change occurs in the process or device in the content filling system 10 or when the content filling system 10 is not used for a certain period. Alternatively, this initial bacteria confirmation method may be periodically performed for each predetermined filling cycle, regardless of whether or not there is a risk of affecting sterility.

First, before performing the initial bacteria confirmation method according to the present embodiment, a test as to whether or not sterility is ensured for each element of the content filling system 10 is individually performed. Specifically, for example, a test as to whether or not a supply line of the content is properly increased in temperature (SIP temperature increase confirmation test), a test as to whether the bottle 30 and the cap 33 are properly sterilized (bottle sterilization test, cap sterilization test), a test as to whether or not the sterile chamber 70 is sterilized (chamber sterilization test), etc. are performed.

After performing such a test, in order to evaluate the sterility of the bottle 30, the initial bacteria confirmation method according to the present embodiment is executed. Specifically, a large number of the bottles 30 are allowed to flow into the content filling system 10, the bottles 30 are not sterilized by the container sterilizer 13 (sterilizer 11), and each of the bottles 30 is filled with a predetermined culture medium instead of the content to be actually filled inside the bottle 30 and is capped with the cap 33. After that, it is confirmed that the culture medium filled inside each of the bottles 30 does not become corrupted after the lapse of a certain period of time (initial bacteria confirmation method for containers).

Hereinafter, the initial bacteria confirmation method (initial bacteria confirmation method for containers) in the content filling system 10 according to the present embodiment will be further described with reference to FIGS. 2 and 3. FIG. 2 is a flowchart showing the initial bacteria confirmation method according to the present embodiment, and FIG. 3 is a schematic plan view illustrating the content filling system when the initial bacteria confirmation method is executed according to the present embodiment. In FIG. 3, the same portions as those in the content filling system 10 illustrated in FIG. 1 will be assigned with the same reference numerals.

First, as illustrated in FIG. 3, the empty bottle 30 for verification is allowed to flow into the content filling system 10. In this case, the empty bottle 30 is fed from the outside to the bottle feeding portion 21 of the content filling system 10 (container feeding process, step S1 in FIG. 2). The number of the bottles 30 is predetermined, and can be set to a predetermined number, for example 100 or more and 300,000 or less (preferably 1,000 or more and 30,000 or less).

Then, the bottle 30 is sent to the sterilizer 11 of the container sterilizer 13. The sterilizer 11 of the container sterilizer 13, the air rinse device 14 and the sterile water rinse device 15 are previously stopped, and sterilization treatment is not performed on the bottle 30. Thus, the bottle 30 is not sterilized by the sterilizer 11, passes through the sterilizer 11, the air rinse device 14 and the sterile water rinse device 15 as it is, and is conveyed to the filling device 20 (nonsterile container conveying process, step S2 in FIG. 2). Instead of passing through the sterilizer 11, the air rinse device 14 and the sterile water rinse device 15, the bottle 30 may be sent to the filling device 20 by using another detour route.

Here, a method of conveying the bottle 30 alone in the sterile chamber 70 without sterilizing the bottle 30 and filling the culture medium with the filling device (filler) 20 as described later will be described. First, in the case of a hydrogen peroxide gas method, in the sterilizer 11, a hydrogen peroxide gas is bypassed so as not to be introduced into the bottle 30, or supply of the hydrogen peroxide gas is stopped. When air is supplied into the bottle 30, the number of initial bacteria in the bottle 30 cannot be accurately measured, so that it is necessary to bypass the air.

Figure 5:
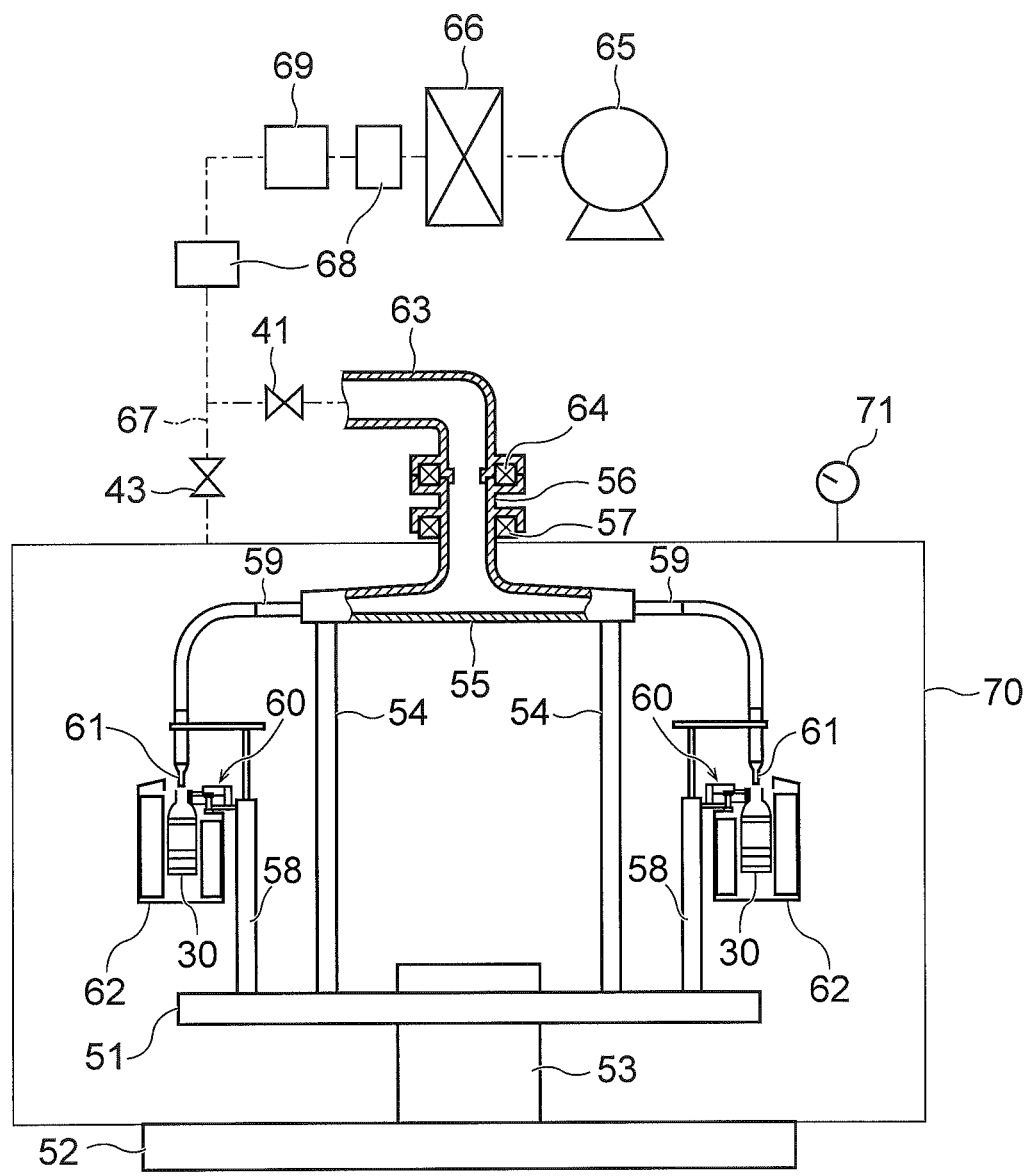
FIG. 5 is a schematic cross-sectional view illustrating a sterilizer of the content filling system used in the initial bacteria confirmation method according to the first embodiment of the present invention.

FIG. 5 is a schematic cross-sectional view illustrating the sterilizer 11. As illustrated in FIG. 5, a wheel 51 rotated by the power from a predetermined drive source is mounted horizontally to a swiveling shaft 53 standing upward from a machine table 52. A column 54 extends upward from the surface of the wheel 51, and a manifold 55 into which the hydrogen peroxide gas flows is fixed to the upper end of the column 54. A conduit 56 extends upward on a line extending from the axis of the swiveling shaft 53 at the upper central portion of the manifold 55, and the conduit 56 is held through a bearing 57 to a frame member of the sterile chamber 70 connected to the machine table 52. Accordingly, the manifold 55 is rotatable around the swiveling shaft 53 integrally with the wheel 51.

In addition, another column 58 extends upward from the surface of the wheel 51, and a gripper 60 of the bottle 30 is attached to the upper portion of the column 58. A large number of the columns 58 and the grippers 60 are each arranged around the wheel 51 at predetermined pitches. A large number of the grippers 60 are coupled with the wheel 51 through the columns 58 and rotate in accordance with the rotation of the wheel 51.

Supply tubes 59 for supplying the hydrogen peroxide gas each extend from a portion around the manifold 55 toward the grippers 60, and nozzles 61 are mounted to the front end portions of the supply tubes 59. The nozzles 61 are fixed to the columns 58, and the openings formed to the front ends of the nozzles 61 are directed to the mouths of the bottles 30 held by the grippers 60. According to this arrangement, when the wheel 51 is rotated, the nozzle 61 is also rotated around the swiveling shaft 53 together with the bottle 30 held by the gripper 60 so as to blow the hydrogen peroxide gas against the bottle 30. Further, tunnels 62 are provided around the wheel 51 so as to surround passing ways of the bottles 30 held by the gripper 60. The nozzle 61 may be provided with a guide member (not illustrated) which discharges the hydrogen peroxide gas introduced into the bottle 30 to the outside of the bottle 30 while bringing the hydrogen peroxide gas into contact with a screw mouth (see FIGS. 4 and 5 of JP 4526820 B1).

A conduit 63 is connected to the upper end of the conduit 56 of the manifold 55 through a seal member 64. The conduit 56 is rotated integrally with the manifold 55 with respect to the conduit 63, and the seal member 64 prevents the hydrogen peroxide gas from leaking through the connection portion between both the conduits 56 and 63. A first valve 41 for controlling passage of the hydrogen peroxide gas in the conduit 63 is attached to the conduit 63. A bypass conduit 67 diverges from the upstream side of the first valve 41. The bypass conduit 67 communicates with the inside of the sterile chamber 70. A second valve 43 for controlling passage of the hydrogen peroxide gas in the bypass conduit 67 is attached to the bypass conduit 67. The bypass conduit 67 may extend from between the bearing 57 and the nozzle 61.

A gas supply device constituted of a blower 65, a High Efficiency Particulate Air Filter (HEPA) filter 66 and an electric heater 69 is disposed on the upstream side of the conduit 63. A hydrogen peroxide addition device 68 is incorporated in one or both of the front and rear sides of the electric heater 69. When the hydrogen peroxide addition device 68 is installed on the downstream of the electric heater 69, it is preferable to mix hydrogen peroxide in a gaseous state in piping. If hydrogen peroxide is not in a gaseous state, a residual value of hydrogen peroxide tends to increase. On the other hand, when the hydrogen peroxide addition device 68 is installed on the upstream of the electric heater 69, hydrogen peroxide in a liquid state such as a spray state may be added in piping. In such a case, although the set temperature of the electric heater 69 is preferably set to be not less than the boiling point of the disinfectant to be supplied, the set temperature may be 100° C. or more (preferably 130° C. or more) depending on the sterilizing strength of the bottle 30. Alternatively, another electric heater may be provided on the further upstream of a spray and sprayed on sterile hot air (80° C. or more). Alternatively, the hydrogen peroxide addition device 68 may be incorporated in both of the front and rear sides of the electric heater 69. When the bottle 30 is formed of polyethylene terephthalate (PET), the hydrogen peroxide tends to be adsorbed, and the residual value tends to increase. However, when the bottle 30 is formed of high density polyethylene (HDPE), the amount of hydrogen peroxide adsorbed is as extremely small as ⅕ to ¹/₂₀. Thus, not only a method of gasifying hydrogen peroxide water and adding the gasified hydrogen peroxide water into sterile air but also a method of spraying hydrogen peroxide water and mixing the hydrogen peroxide water with air may be adopted. The hydrogen peroxide gas is blown from the nozzle 61 to the bottle 30 through each of the supply tubes 59 to sterilize the bottle 30. A pressure gauge 71 for measuring the pressure in the sterile chamber 70 is attached to the sterile chamber 70. The disinfectant only has to be one containing hydrogen peroxide with a concentration of 1% or more. Hydrogen peroxide water having a concentration of 35% diluted with ethanol may be used.

In FIG. 5, during normal production, while the first valve 41 of the sterilizer 11 is opened, the second valve 43 is capped, whereby hydrogen peroxide gas is introduced into the bottle 30 through the commonly used conduit 63. On the other hand, in a case where confirmation operation of initial bacteria in the container is performed, while the first valve 41 is capped, the second valve 43 on the bypass side is opened. As a result, the hydrogen peroxide gas passes through the bypass conduit 67, so that the hydrogen peroxide gas is not introduced into the bottle 30. In a case where confirmation operation of initial bacteria in the container is performed, while the first valve 41 may be opened, the second valve 43 on the bypass side may be opened.

Similarly, in the next air rinsing process using the air rinse device 14, it is necessary to bypass sterile air or to stop supply of the sterile air so as not to replace the interior of the bottle 30 with the sterile air. However, it is preferable that the sterile air is supplied into the sterile chamber 70 in the same manner as in normal production so that germs are not mixed into the sterile chamber 70 in a positive pressure state. The configuration of the air rinse device 14 may be substantially the same as that of the sterilizer 11 illustrated in FIG. 5.

In the case of a facility equipped with the sterile water rinse device 15 as in the present embodiment, an accurate number of initial bacteria cannot be ascertained when the bottle 30 is washed with sterile water, so that it is necessary to reduce the flow rate of the sterile water to such an extent that the sterile water does not come into contact with the bottle 30. When dry operation of a machine is performed with the sterile water rinse stopped, a distributor of the sterile water rinse device 15 may wear out and be damaged, and therefore, it is preferable to minimize the flow rate while supplying sterile water (for example, the flow rate per nozzle is 3 L/min or less). The same idea may be used in the case of a drug rinse method using a peracetic acid formulation.

Subsequently, in the filling device 20, a predetermined amount of culture medium is filled inside the bottle 30 from the mouth of the bottle 30 (culture medium filling process, step S3 in FIG. 2).

The culture medium is previously prepared before filled inside the bottle 30 by the filling device 20, and heating sterilization treatment is performed. The characteristics of the culture medium are matched to the characteristics of the content to be filled in the content filling system 10, the characteristics influencing propagation of bacteria. In the present embodiment, pH of the culture medium is adjusted to be acidic according to pH of the content, and, for example, the pH is 4.0 or more and 4.6 or less. More specifically, when the pH of the content is less than pH 4.0, it is preferable that the pH of the culture medium is adjusted to pH 4.0 which is the upper limit. When the pH of the content is pH 4 or more and less than 4.6, it is preferable that the pH of the culture medium is adjusted to pH 4.6 which is the upper limit. On the other hand, when the standard of the product having the highest pH among the product bottles 35 to be produced has a pH of, for example, 3.5±0.2, the pH of the culture medium is adjusted to pH 3.5, or pH 3.7 which is the upper limit value, or pH 3.8 or pH 3.9 which is slightly higher than the upper limit value, and the test may be carried out.

Thus, when the pH of the culture medium is adjusted to 3.5 or more and 4.6 or less, preferably 4.0 or more and 4.6 or less so as to be matched to the characteristics of the content, the culture medium provides an environment allowing survival of bacterial spores but not allowing survival of vegetative cells of bacteria, mold and yeast. Thus, the growing environment of bacteria in the culture medium can be resembled the content to be actually filled.

Such a culture medium is generally formed by dissolving in water 0.2 to 3% by weight of glucose which is an organic carbon source, monosaccharides such as dextrose, disaccharides, polysaccharides, sodium carbonate, which is an inorganic carbon source, or sodium bicarbonate as a carbon source, 0.5 to 3% by weight of casein peptone, chicken peptone, cardiac muscle peptone, gelatin peptone, soybean peptone, polypeptone, yeast extract, meat extract, ammonium sulfate, magnesium sulfate, nitrate or the like as a nitrogen source (including coenzyme), and 0.05 to 1% by weight of sodium chloride, monopotassium phosphate, potassium monohydrogenphosphate, potassium dihydrogenphosphate or the like as a trace mineral or a buffering agent. The pH of the culture medium is adjusted by dissolving hydrochloric acid, tartaric acid, citric acid, sodium hydroxide, potassium hydroxide or the like in the culture medium.

The culture medium is subjected to heat sterilization (UHT) or filter sterilization by a prescribed sterilization method in a liquid treatment facility 23 and filled by the filling device 20. When carbonate drinks are also produced by the liquid treatment facility 23, a carbon dioxide dissolving device (carbonator) 24 which adds filter sterilized carbonic acid gas to a product liquid is required to be installed before the filling device 20. When the culture medium is filled, addition of carbonic acid gas may result in a bacteriostatic culture medium, and therefore, supply of the carbonic acid gas may be stopped, or the carbonic acid gas may be replaced with air. When the carbonic acid gas is changed to air, it is also possible to confirm sterility including a filtration filter of a carbon dioxide sterile facility (not illustrated).

Subsequently, the bottle 30 filled with the culture medium passes under a gas replacement device 25, which replaces gas in a head space in the bottle 30, from the filling device 20, and is sent to the cap attachment device 16. The gas replacement device 25 blows filter sterilized inert gas (nitrogen or carbon dioxide) into the mouth of the bottle 30 in normal production, and may stop supply of the inert gas (nitrogen or carbon dioxide) or replace the inert gas with air when filling the culture medium. When the inert gas is changed to air, it is also possible to confirm sterility including a filtration filter of the gas replacement device 25 in the head space.

On the other hand, the cap 33 is previously sterilized by the cap sterilizer 18 (cap sterilization process, step S8 in FIG. 2). The cap 33 is carried into the cap sterilizer 18 from the outside of the content filling system 10, the mist or gas of hydrogen peroxide is blown against the cap 33 to sterilize the inner and outer surfaces of the cap 33, hydrogen peroxide is removed while activated with hot air, and then the cap 33 is washed with sterile water and sent to the cap attachment device 16. The cap sterilization process is executed in the same manner as the cap sterilization process in the ordinary content filling method described above.

Subsequently, in the cap attachment device 16, the sterilized cap 33 sterilized by the cap sterilizer 18 is attached to the mouth of the bottle 30 (cap attaching process, step S4 in FIG. 2). The cap attaching process is executed in the same manner as the cap attaching process in the ordinary content filling method described above. In this way, the culture medium is filled inside the bottle 30, and the mouth is tightly capped with the cap 33, whereby a verification bottle 36 is obtained.

Then, the verification bottle 36 filled with the culture medium is carried from the product bottle conveyor 22 to the outside, and packaged in a packaging process. A case with packaged bottles is manually or automatically tilted (or reversed) on a conveyor to reliably bring the culture medium into contact with the inner surface of the bottle 30 (culture medium contact process, step S5 in FIG. 4). Thereafter, a plurality of the verification bottles 36 is conveyed to a constant temperature storage 37 maintained at a predetermined temperature of 25° C. or more and 40° C. or less, and is allowed to stand still in the constant temperature storage 37 and cultured (culture process, step S6 in FIG. 2). When the product bottle 35 is warmed and sold by a hot bender or the like, it is preferable to confirm sterility against thermophilic bacteria, and the verification bottle 36 may be cultured at a temperature of 40° C. or more and 65° C. or less in addition to the above culture conditions.

After a lapse of a predetermined period (for example, three days or more, preferably seven days or more), all the verification bottles 36 are taken out from the constant temperature storage 37, and whether or not bacteria survive or propagate in the culture medium in the verification bottle 36 is verified (verifying process, step S7 in FIG. 2). As a result of this verification, if the number of the verification bottles 36 in which the bacteria survive or propagate is not more than a predetermined number (for example, zero), it is judged that the bottle 30 has no initial bacteria and sterility is ensured. On the other hand, as a result of the verification, if the number of the verification bottles 36 in which the bacteria survive or propagate is not less than a predetermined number (for example, one or more), it is judged that the bottle 30 has initial bacteria, and measures are taken. For example, the conveyance path and carrying-in path for the bottle 30 may be sterilized, or sterilization conditions in the container sterilizer 13 (sterilizer 11) may be adjusted (strengthened). Depending on the type of bacteria, it may be possible to sufficiently sterilize the bottle 30 by operating the container sterilizer 13 (sterilizer 11). In this case, it can be judged that when the bottle 30 is actually filled with a content such as a beverage, the container sterilizer 13 only has to be operated.

In order to shorten the period during which the culture medium in the verification bottle 36 is cultured in the constant temperature storage 37, physical movement is added to the culture medium in the verification bottle 36, and the verification bottle 36 may be stored in a state in which the culture medium is moving. Such movements include, for example, rotation, inversion, reciprocation, vibration, stirring, and the like. Since penetration of oxygen into the culture medium is promoted by adding physical movement to the culture medium, bacteria are cultured aerobically, whereby culture speed of the bacteria can be increased. As a result, it becomes possible to shorten the predetermined period (for example, three days or more, preferably seven days or more) necessary for culture, and it is possible to promptly judge whether or not the initial bacteria are generated in the bottle 30.

For example, according to the experiments of the inventors of the present invention, it has been found that when vibration is applied to the bottle 30, filled with the culture medium, in the constant temperature storage 37 (Example A), culture of bacteria can be further promoted as compared with the case where no vibration is applied to the bottle 30 (Comparative Example B). Specifically, a plurality of the bottles 30 each filled with a liquid neutral medium was capped in a state of including falling bacteria floating in a laboratory in the head space of the bottle 30, and stored at 22° C. to 27° C. Meanwhile, vibration was applied to the bottles 30 (Example A) of one group, and the bottles 30 (Comparative Example B) of another group were allowed to stand still without undergoing vibration. As a result, as shown in the table below, the positive rate increased especially during 2 to 3 days of culture days. This indicates that bacteria can be cultured in a shorter number of days by adding vibration, as compared with the case of applying no vibration. Here, the positive rate refers to the ratio of the number of the bottles 30 which are positive at a predetermined time to the number (total number of positive bottles) of the bottles 30 in which bacteria finally survive or propagate (become positive). Specifically, the positive rate is calculated based on the expression "positive rate (%)= (number of bottles that could be visually confirmed as being positive/total number of positive bottles)×100". The total number of positive bottles was defined as the number of bottles that could be visually confirmed as being positive after 13 days of culture.

TABLE 1

| Positive rate | 0 days | 2 days | 3 days | 7 days |
| --- | --- | --- | --- | --- |
| Example A (with vibration) | 0% | 30% | 86% | 100% |
| Comparative Example B (no vibration) | 0% | 18% | 33% | 100% |

As described above, according to the present embodiment, the bottle 30 which is not sterilized by the container sterilizer 13 is filled with the culture medium and capped with the cap 33, and then whether or not bacteria survive or propagate in the culture medium in the bottle 30 is verified. Consequently, it is possible to accurately grasp bioburden as to whether or not initial bacteria are generated in the bottle 30, and to take measures against sterilization of the bottle 30 before actually filling the bottle 30 with a content such as a beverage.

According to the present embodiment, since the pH of the culture medium used for the verification is adjusted to 4.0 or more and 4.6 or less according to an acidic content to be actually filled, the culture medium allows survival of bacterial spores but does not allow survival of vegetative cells of bacteria, mold and yeast. Consequently, when the sterility of the content filling system 10 is comprehensively evaluated using the culture medium, verification can be performed such that the growing environment of bacteria is resembled the actual content. Thus, no excessive facilities for sterilization are necessary, and it is possible to reduce medicines and heat energy required for sterilization, so that the production cost of the product bottle 35 can be reduced. For example, it is possible to reduce the temperature of steam, hot water or the like used for Sterilizing in Place (SIP) treatment in a beverage supply system piping of the content filling system 10, or to shorten the time for flowing steam, hot water, or the like. In addition, it is possible to shorten the time required to perform Cleaning out of Place (COP) treatment or Sterilizing out of Place (SOP) treatment in the sterile chamber 70.

When the content to be actually filled is a low acidic or neutral beverage, the pH of the culture may range from as low acidic as 7.0 (6.0 or more and 8.0 or less) to neutral, similarly to a general culture medium. In this case, almost all the bacteria can be detected.

In the above case, although the sterilizer performing hydrogen peroxide sterilization and hot water sterilization is used as the sterilizer for the container, the present invention is not limited thereto. It is possible to adopt all sterilizers such as a sterilizer using a peracetic acid sterilization method of sterilizing an inner and outer surfaces of the bottle with peracetic acid rinse and then rinsing the inner and outer surfaces with sterile water, a sterilizer using an electron beam sterilization method of applying an electron beam to the inner or outer surface of the bottle and then performing air-rinsing with sterile air, and a sterilizer using UV sterilization. In addition to sterilizing bottles, the sterilizer may be used for sterilizing preforms, cups, pouches, and paper containers. In the above example, since a PET bottle is used as the container, a culture medium for aerobic bacteria is used; however, the culture medium is not limited to this. When a retort container such as canned food is used, a culture medium for anaerobic bacteria may be used.

(Modification)

Next, a modification of the present embodiment will be described.

In the above-described embodiment, the case of verifying whether or not initial bacteria are generated in the bottle 30 has been described as an example. However, the present invention is not limited to this, and it may be verified whether or not initial bacteria are generated in the cap 33. That is, a large number of the bottles 30 are allowed to flow into the content filling system 10, and each of the bottles 30 is sterilized. Thereafter, each of the bottles 30 is filled with a predetermined culture medium instead of the content to be actually filled inside each of the bottles 30. Then, the bottle 30 is capped with the cap 33 which is not sterilized by the cap sterilizer 18. After that, it is confirmed that the culture medium filled inside each of the bottles 30 does not become corrupted after the lapse of a certain period of time (initial bacteria confirmation method for caps).

Figure 4:
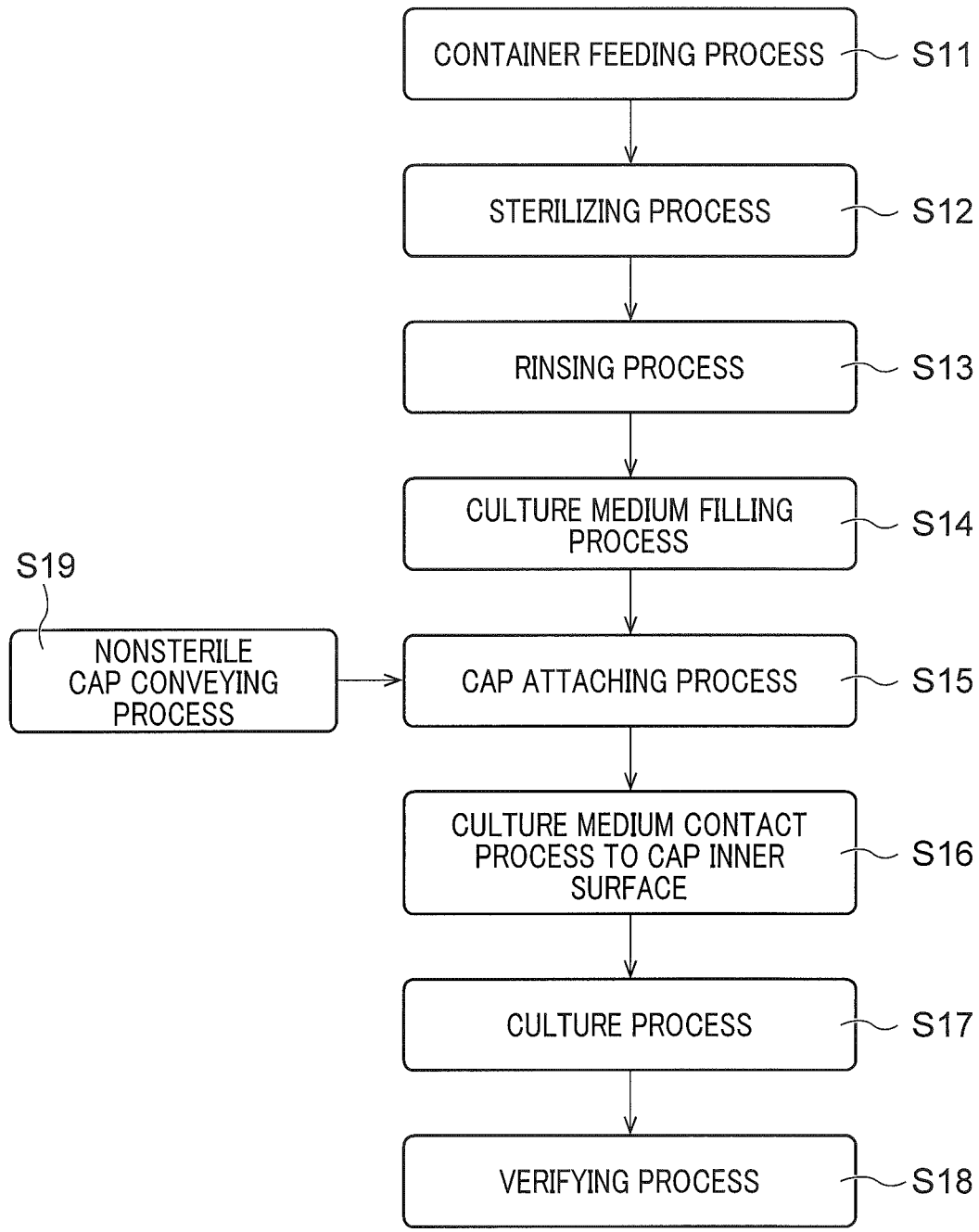
FIG. 4 is a flowchart illustrating an initial bacteria confirmation method according to a modification of the first embodiment of the present invention.

Hereinafter, the initial bacteria confirmation method (initial bacteria confirmation method for caps) in the content filling system 10 according to the present modification will be described with reference to FIGS. 3 and 4. FIG. 4 is a flowchart illustrating the initial bacteria confirmation method according to the modification.

First, similarly to the above, the empty bottle 30 for verification is allowed to flow into the content filling system 10. In this case, the empty bottle 30 is fed from the outside to the bottle feeding portion 21 of the content filling system 10 (container feeding process, step S11 in FIG. 4). The number of the bottles 30 is predetermined, and can be set to a predetermined number, for example 1,000 or more and 300,000 or less (preferably 3,000 or more and 30,000 or less).

Then, the bottle 30 is sent to the sterilizer 11 of the container sterilizer 13, and in the sterilizer 11, the bottle 30 is sterilized using a hydrogen peroxide aqueous solution as a disinfectant (sterilization process, step S12 in FIG. 4). The sterilization process is executed in the same manner as the sterilization process in the ordinary content filling method described above.

Subsequently, the bottle 30 is sequentially sent to the air rinse device 14 and the sterile water rinse device 15, and in the air rinse device 14 and the sterile water rinse device 15, the bottle 30 is washed with air and sterile water (rinsing process, step S13 in FIG. 4). This rinsing process is similar to the rinsing process in the ordinary content filling method described above.

Then, the bottle 30 is conveyed to the filling device 20. In the filling device 20, a predetermined amount of sterilized culture medium is filled inside the bottle 30 from the mouth of the bottle 30 (culture medium filling process, step S14 in FIG. 4). This culture medium filling process is similar to the culture medium filling process in the initial bacteria confirmation method for containers described above.

On the other hand, the cap sterilizer 18 is previously stopped, and sterilization treatment is not performed on the cap 33. Thus, the cap 33 passes through the cap sterilizer 18 as it is without being sterilized by the cap sterilizer 18, and is conveyed to the cap attachment device 16 (nonsterile cap conveying process, step S18 in FIG. 4). Instead of passing through the cap sterilizer 18, the cap 33 may be sent to the cap attachment device 16 by using another detour route.

Subsequently, the bottle 30 filled with the culture medium is sent to the cap attachment device 16. In the cap attachment device 16, the cap 33 which is not sterilized is attached to the mouth of the bottle 30 (cap attaching process, step S15 in FIG. 4). In this way, the culture medium is filled inside the bottle 30, and the mouth is tightly capped with the nonsterile cap 33, whereby the verification bottle 36 is obtained.

Then, the verification bottle 36 filled with the culture medium is carried from the product bottle conveyor 22 to the outside, and packaged in a packaging process. A case with packaged bottles is manually or automatically tilted (or reversed) on a conveyor to reliably bring the culture medium into contact with the inner surface of the cap 33 (culture medium contact process, step S16 in FIG. 4). Thereafter, a plurality of the verification bottles 36 is conveyed to the constant temperature storage 37, and is allowed to stand still in the constant temperature storage 37 and cultured (culture process, step S17 in FIG. 4). This culture process is similar to the culture process in the initial bacteria confirmation method for containers described above.

After a lapse of a predetermined period (for example, three days or more, preferably seven days or more), all the verification bottles 36 are taken out from the constant temperature storage 37, and whether or not bacteria survive or propagate in the culture medium in the verification bottle 36 is verified (verifying process, step S18 in FIG. 4). As a result of this verification, it is possible to accurately grasp the actual bioburden of the cap. On the other hand, as a result of the verification, if the number of the verification bottles 36 in which the bacteria survive or propagate is not less than a predetermined number (for example, one or more), it is judged that the cap 33 has initial bacteria, and measures are taken. For example, the conveyance path and carrying-in path for the cap 33 may be sterilized, or sterilization conditions in the cap sterilizer 18 may be adjusted (strengthened). Depending on the type of bacteria, it may be possible to sufficiently sterilize the cap 33 by operating the cap sterilizer 18. In this case, it can be judged that when the bottle 30 is actually filled with a content such as a beverage, the cap sterilizer 18 only has to be operated.

As described above, according to the present modification, the sterilized bottle 30 is filled with the culture medium and capped with the cap 33 which is not sterilized by the cap sterilizer 18, and then whether or not bacteria survive or propagate in the culture medium in the bottle 30 is verified.

Consequently, it is possible to accurately grasp whether or not initial bacteria are generated in the cap 33, and to take measures against sterilization of the cap 33 before actually filling the bottle 30 with a content such as a beverage.

Whether or not initial bacteria is generated in the bottle 30 or the cap 33 may be verified at once by combining the first embodiment and the modification. That is, the bottle 30 is conveyed to the filling device 20 without being sterilized by the container sterilizer 13, and the sterilized culture medium is filled inside the non-sterilized bottle 30 by using the filling device 20. Subsequently, the cap 33 is conveyed to the cap attachment device 16 without being sterilized by the cap sterilizer 18, and the bottle 30 is capped with the not-sterilized cap 33 by using the cap attachment device 16. Thereafter, whether or not bacteria survive or propagate in the culture medium in the bottle 30 may be verified.

Examples

Next, a specific example of the first embodiment will be described.

Example 1-1

A 600 bottle per minute (bpm) beverage filling system was used in which a sterilized beverage was filled at room temperature into a 500 mL capacity PET bottle sterilized in a sterile atmosphere and the PET bottle was sealed with a sterilized cap. Using this beverage filling system, 3,000 PET bottles which would not be sterilized were filled with sterilized acidic culture medium of pH 4.0 at room temperature and each capped with a sterilized cap. Then, these PET bottles were cultured at 27° C. for 1 week, and then all of the PET bottles were inspected. As a result, only one PET bottle with a corrupted culture medium was present. As a result of identification of bacteria contained in the corrupted culture medium, a bacterium with low drug resistance (*Cladosporium cladosporioides*) was confirmed. Thus, when a beverage was actually filled inside the PET bottle, it was judged that the PET bottle could be sufficiently sterilized by operating a container sterilizer.

Example 1-2

A 600 bottle per minute (bpm) beverage filling system was used in which a sterilized beverage was filled at room temperature into a 500 mL capacity PET bottle sterilized in a sterile atmosphere and the PET bottle was sealed with a sterilized cap. Using this beverage filling system, 3,000 sterilized PET bottles were filled with sterilized acidic culture medium of pH 4.0 at room temperature and each capped with a cap which was not sterilized. Then, these PET bottles were cultured at 27° C. for 1 week, and then all of the PET bottles were inspected. As a result, only one PET bottle with a corrupted culture medium was present. As a result of identification of bacteria contained in the corrupted culture medium, the bacteria were presumed to be *A. niger*. Thus, when a beverage was actually filled inside the PET bottle, it was judged that the PET bottle could be sufficiently sterilized by operating a cap sterilizer.

Second Embodiment

Figure 6:
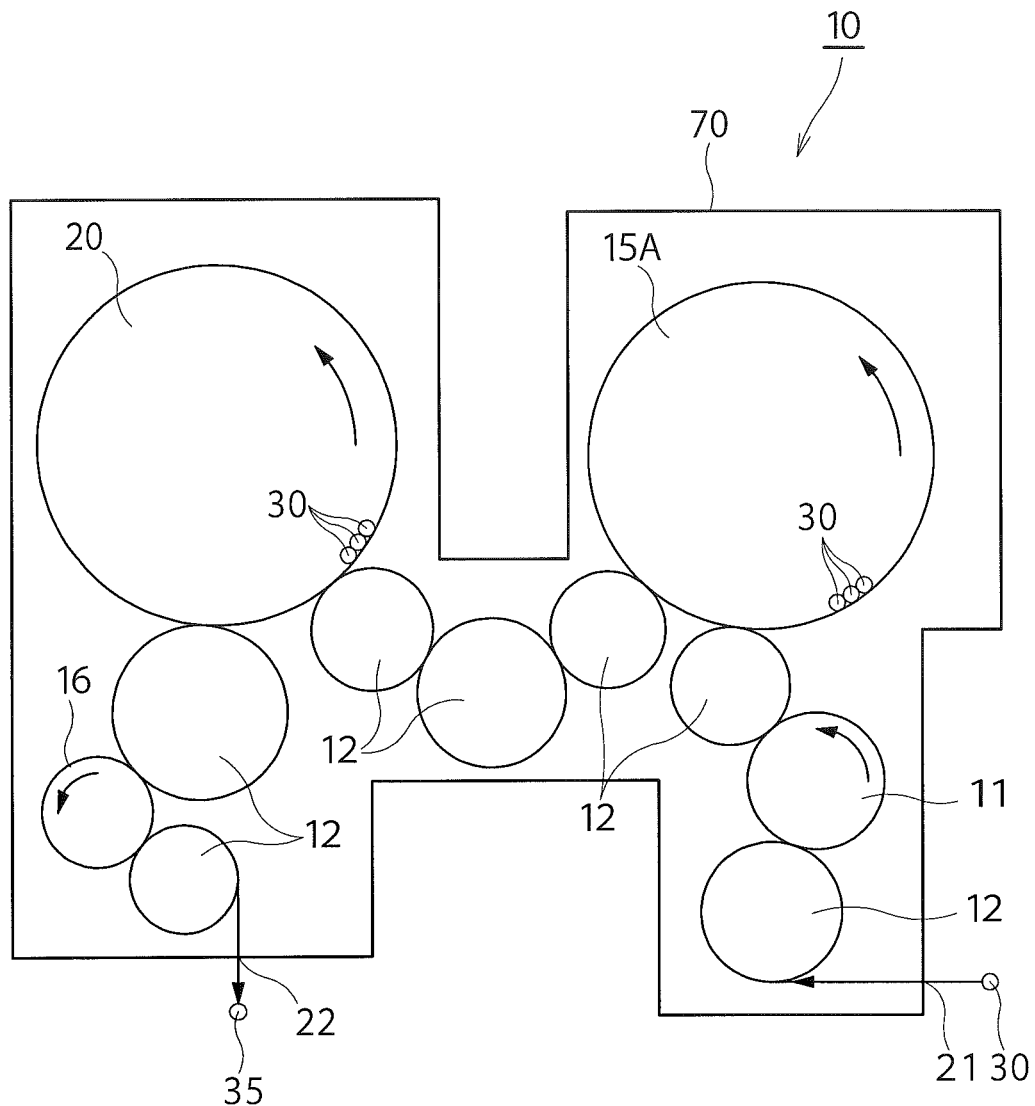
FIG. 6 is a schematic plan view illustrating a content filling system used in a verification method according to a second embodiment of the present invention.
Figure 7:
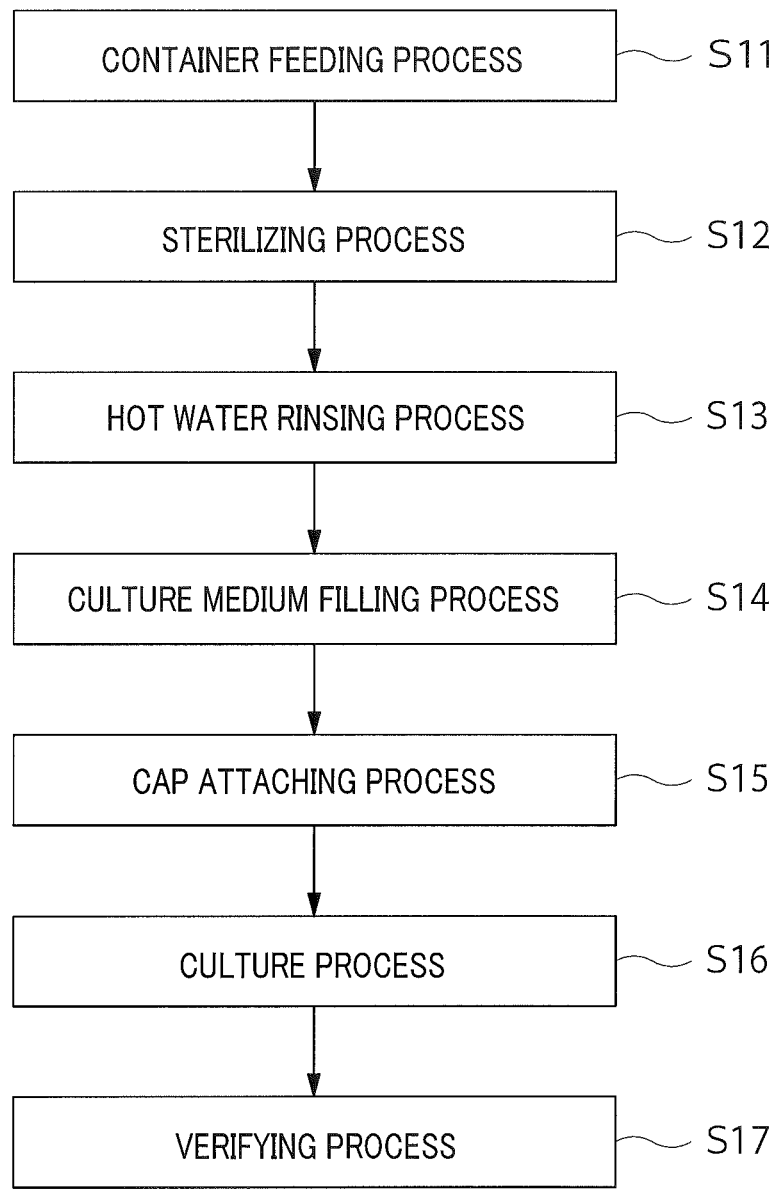
FIG. 7 is a flowchart showing the verification method according to the second embodiment of the present invention.
Figure 8:
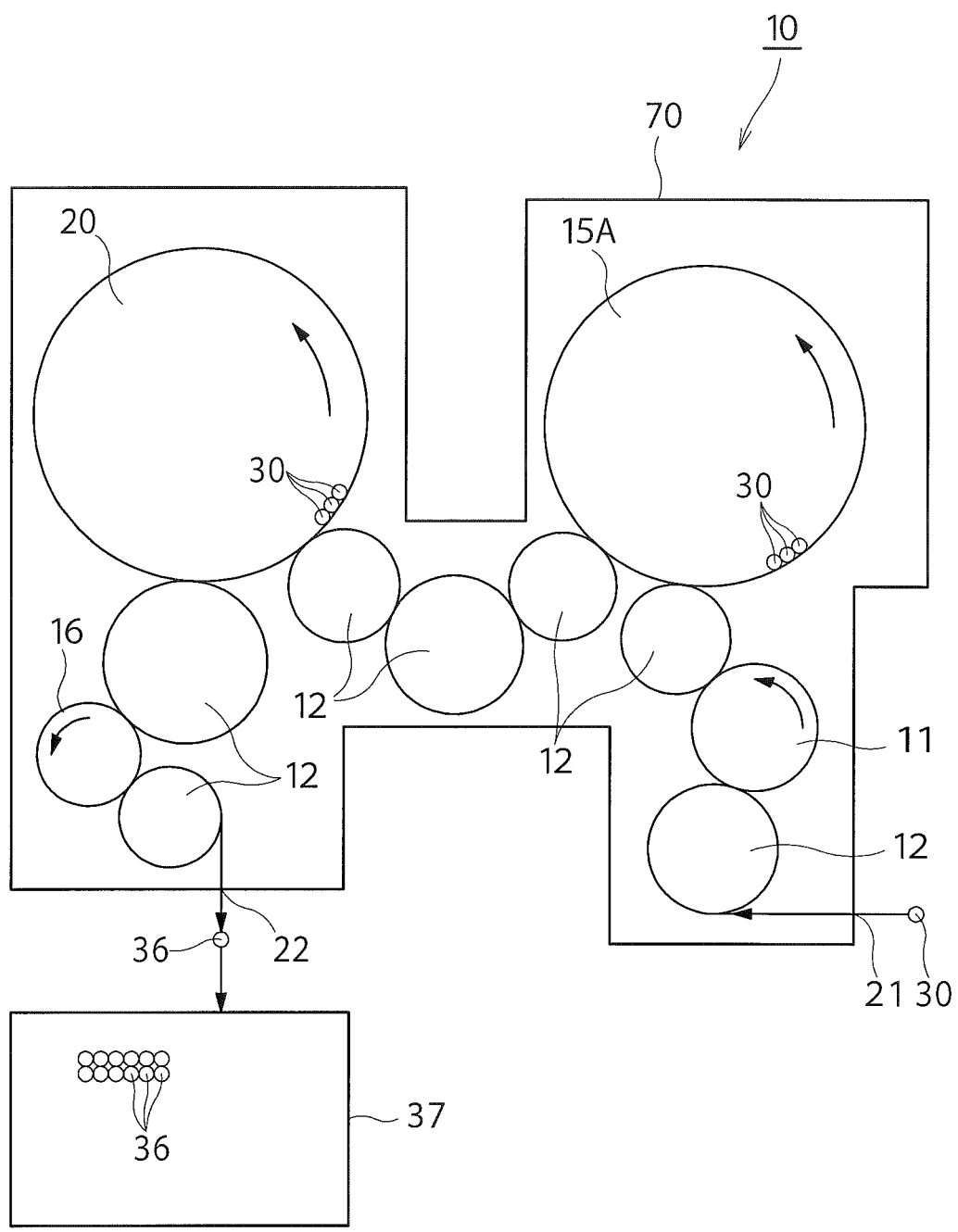
FIG. 8 is a schematic plan view illustrating the content filling system when the verification method is executed according to the second embodiment of the present invention.

Next, a second embodiment of the present invention will be described below with reference to the drawings. FIGS. 6 to 8 illustrate the second embodiment of the present invention. In FIGS. 6 to 8, the same portions as those in the first embodiment illustrated in FIGS. 1 to 5 will be assigned with the same reference numerals and will not be described in detail.

(Content Filling System)

First, a content filling system (sterile filling system, aseptic filling system) according to the present embodiment will be described with reference to FIG. 6.

A content filling system 10 illustrated in FIG. 6 includes a bottle feeding portion 21, a sterilizer 11, a hot water rinse device 15A, a filling device (filler) 20, a cap attachment device (a capper, a seamer, and a capping machine) 16, and a product bottle conveyor 22. These bottle feeding portion 21, sterilizer 11, hot water rinse device 15A, filling device 20, cap attachment device 16, and product bottle conveyor 22 are disposed in this order along a conveying direction thereof from an upstream side to a downstream side. Between the sterilizer 11, the hot water rinse device 15A, the filling device 20, and the cap attachment device 16, a plurality of convey wheels 12 for conveying a bottle 30 between these devices is provided.

The hot water rinse device 15A sterilizes the bottle 30, sterilized by a hydrogen peroxide aqueous solution as a disinfectant, with hot water. Specifically, for example, hot water having a temperature of 65° C. or more and 80° C. or less is supplied into the bottle 30.

The content filled from the filling device 20 has a predetermined characteristic influencing propagation of bacteria. In the present embodiment, the predetermined characteristic is pH of the content. More specifically, the content is an acid beverage. The acidity of the beverage is preferably less than pH 4.6, more preferably less than pH 4.0.

A sterile chamber 70 houses the sterilizer 11, the hot water rinse device 15A, the filling device 20, and the cap attachment device 16, which have been described above. This content filling system 10 may be, for example, a sterile filling system. In this case, the interior of the sterile chamber 70 is kept in a sterile state.

In the present embodiment, since the configurations of the bottle feeding portion 21, the sterilizer 11, the filling device 20, the cap attachment device 16, and the product bottle conveyor 22 are substantially the same as the configurations in the first embodiment, detailed descriptions thereof will be omitted here.

(Content Filling Method)

Next, a content filling method using the above-described content filling system 10 (FIG. 6) will be described. In the following description, a filling method at a normal time, that is, a content filling method in which a content such as a beverage is actually filled inside the bottle 30 to produce the product bottle 35 will be described.

First, the plurality of empty bottles 30 is sequentially fed from the outside of the content filling system 10 to the bottle feeding portion 21. The bottle 30 is sent from the bottle feeding portion 21 to the sterilizer 11 by the convey wheel 12 (container feeding process).

Then, in the sterilizer 11, the bottle 30 is sterilized using a hydrogen peroxide aqueous solution as a disinfectant (sterilization process). This sterilization process is substantially the same as the sterilization process in the first embodiment.

Subsequently, the bottle 30 is conveyed to the hot water rinse device 15A by the convey wheel 12. In the hot water rinse device 15A, the bottle 30 sterilized by hydrogen peroxide as a disinfectant is sterilized with hot water (hot water rinsing process). Specifically, hot water at a temperature of 65° C. or more and 75° C. or less is supplied into the bottle 30 at a flow rate of 5 L/min or more and 15 L/min or less. At this time, it is preferable that the bottle 30 takes an inverted attitude, and the hot water is supplied into the bottle 30 through the downwardly opened mouth, and flows out of the bottle 30 from the mouth. With this hot water, mold, yeast, vegetative cells of bacteria, and the like damaged by hydrogen peroxide are sterilized. In addition, an excess hydrogen peroxide aqueous solution remaining in the bottle 30 is washed off with this hot water, and discharged from the bottle 30 outward. In some cases, the hot water rinse may be performed on the outer surface of the bottle 30 as well as the inner surface.

Subsequently, the bottle 30 is conveyed to the filling device 20 by the convey wheel 12. In the filling device 20, while the bottle 30 is rotated (revolved), the content is filled inside the bottle 30 from the mouth (filling process).

The content is previously prepared before filled inside the bottle 30 by the filling device 20, and heating sterilization treatment is performed. As described above, the content has a predetermined pH as a characteristic influencing propagation of bacteria. Specifically, the content is an acid beverage preferably having pH of less than 4.6, more preferably pH of less than 4. This filling process is substantially the same as the filling process in the first embodiment.

Subsequently, the bottle 30 filled with the content is conveyed to the cap attachment device 16 by the convey wheel 12. Subsequently, the cap attachment device 16 attaches an unillustrated sterilized cap to the mouth of the bottle 30, so that it is possible to obtain the product bottle 35 (cap attaching process).

Thereafter, the product bottle 35 is conveyed from the cap attachment device 16 to the product bottle conveyor 22 and is carried toward the outside of the content filling system 10.

(Method for Verifying Content Filling System)

Next, a verification method for verifying the sterility of the above-described content filling system 10 (FIG. 6) will be described.

In the verification method according to the present embodiment, whether or not the sterility of the content filling system 10 is ensured is confirmed. This verification method may be performed, for example, at an early stage immediately after completion of the content filling system 10, that is, before filling the bottle 30 by actually using the content filling system 10 and starting production of the product bottle 35. Alternatively, the verification method according to the present embodiment may be performed when there is a risk of affecting sterility, such as when some change occurs in the process or device in the content filling system 10 or when the content filling system 10 is not used for a certain period. Alternatively, this verification method may be periodically performed for each predetermined filling cycle, regardless of whether or not there is a risk of affecting sterility.

First, before performing the verification method according to the present embodiment, a test as to whether or not sterility is ensured for each element of the content filling system 10 is individually performed. Specifically, for example, a test as to whether or not a supply line of the content is properly increased in temperature (SIP temperature increase confirmation test), a test as to whether the bottle 30 and the cap are properly sterilized (bottle sterilization test, cap sterilization test), a test as to whether or not the sterile chamber 70 is sterilized (chamber sterilization test), etc. are performed. These tests can be carried out by conventionally known methods.

In order to comprehensively evaluate the sterility of the content filling system 10 at a final stage after such tests, the verification method according to the present embodiment using the bottle 30 filled with a culture medium is executed. Specifically, a large number of the bottles 30 are allowed to flow into the content filling system 10, and each of the bottles 30 is filled with a predetermined culture medium instead of the content to be actually filled inside each of the bottles 30, and capped. After that, it is confirmed that the culture medium filled inside each of the bottles 30 does not become corrupted after the lapse of a certain period of time.

Hereinafter, the verification method in the content filling system 10 according to the present embodiment will be further described with reference to FIGS. 7 and 8. FIG. 7 is a flowchart showing the verification method according to the present embodiment, and FIG. 8 is a schematic plan view illustrating the content filling system when the verification method is executed according to the present embodiment. In FIG. 8, the same portions as those in the content filling system 10 illustrated in FIG. 6 will be assigned with the same reference numerals.

First, as illustrated in FIG. 8, the empty bottle 30 for verification is allowed to flow into the content filling system 10. In this case, the empty bottle 30 is fed from the outside to the bottle feeding portion 21 of the content filling system 10 (container feeding process, step S11 in FIG. 7). The number of the bottles 30 is predetermined, and can be set to a predetermined number, for example 1,000 or more and 300,000 or less (preferably 3,000 or more and 30,000 or less).

Then, the bottle 30 is sent to the sterilizer 11, and in the sterilizer 11, the bottle 30 is sterilized using a hydrogen peroxide aqueous solution as a disinfectant (sterilization process, step S12 in FIG. 7). The sterilization process is executed in the same manner as the sterilization process in the ordinary content filling method described above.

Subsequently, the bottle 30 is sent to the hot water rinse device 15A and sterilized with hot water in the hot water rinse device 15A (hot water rinsing process, step S13 in FIG. 7). This hot water rinsing process is similar to the hot water rinsing process in the ordinary content filling method described above.

Then, the bottle 30 is conveyed to the filling device 20. In the filling device 20, a predetermined amount of culture medium is filled inside the bottle 30 from the mouth of the bottle 30 (culture medium filling process, step S14 in FIG. 7).

The culture medium is previously prepared before filled inside the bottle 30 by the filling device 20, and heating sterilization treatment is performed. The characteristics of the culture medium are matched to the characteristics of the content to be filled in the content filling system 10, the characteristics influencing propagation of bacteria. In the present embodiment, pH of the culture medium is adjusted to be acidic according to pH of the content, and, for example, the pH is 4.0 or more and 4.6 or less. More specifically, when the pH of the content is less than pH 4.0, it is preferable that the pH of the culture medium is adjusted to pH 4.0 which is the upper limit. When the pH of the content is pH 4 or more and less than 4.6, it is preferable that the pH of the culture medium is adjusted to pH 4.6 which is the upper limit. On the other hand, when the standard of the product having the highest pH among the product bottles 35 to be produced has a pH of, for example, 3.5±0.2, the pH of the culture medium is adjusted to pH 3.5, or pH 3.7 which is the upper limit value, or pH 3.8 or pH 3.9 which is slightly higher than the upper limit value, and a sterile verification test may be carried out.

Thus, when the pH of the culture medium is adjusted to 3.5 or more and 4.6 or less, preferably 4.0 or more and 4.6 or less so as to be matched to the characteristics of the content, the culture medium provides an environment allowing survival of bacterial spores but not allowing survival of vegetative cells of bacteria, mold and yeast. Thus, the growing environment of bacteria in the culture medium can be resembled the content to be actually filled.

Such a culture medium is generally formed by dissolving in water 0.2 to 3% by weight of glucose which is an organic carbon source, monosaccharides such as dextrose, disaccharides, polysaccharides, sodium carbonate, which is an inorganic carbon source, or sodium bicarbonate as a carbon source, 0.5 to 3% by weight of casein peptone, chicken peptone, cardiac muscle peptone, gelatin peptone, soybean peptone, polypeptone, yeast extract, meat extract, ammonium sulfate, magnesium sulfate, nitrate or the like as a nitrogen source (including coenzyme), and 0.05 to 1% by weight of sodium chloride, monopotassium phosphate, potassium monohydrogenphosphate, potassium dihydrogenphosphate or the like as a trace mineral or a buffering agent. The pH of the culture medium is adjusted by dissolving hydrochloric acid, tartaric acid, citric acid, sodium hydroxide, potassium hydroxide or the like in the culture medium.

In the present embodiment, there is also provided a culture medium which is to be used in such a verification method and has characteristics matched to the characteristics of the content to be filled in the content filling system 10.

Subsequently, the bottle 30 filled with the culture medium is sent to the cap attachment device 16. In the cap attachment device 16, a sterilized cap is attached to the mouth of the bottle 30 (cap attaching process, step S15 in FIG. 7). The cap attaching process is executed in the same manner as the cap attaching process in the ordinary content filling method described above. In this way, the culture medium is filled inside the bottle 30, and the mouth is tightly capped with the cap, whereby the verification bottle 36 is obtained.

Then, the verification bottle 36 filled with the culture medium is carried from the product bottle conveyor 22 to the outside. Thereafter, a plurality of the verification bottles 36 is conveyed to a constant temperature storage 37 maintained at a predetermined temperature of 25° C. or more and 40° C. or less, and is allowed to stand still in the constant temperature storage 37 and cultured (culture process, step S16 in FIG. 7). When the product bottle 35 is warmed and sold by a hot bender or the like, it is necessary to confirm sterility against thermophilic bacteria, and the verification bottle 36 is cultured at a temperature of 40° C. or more and 65° C. or less.

After a lapse of a predetermined period (for example, three days or more, preferably seven days or more), all the verification bottles 36 are taken out from the constant temperature storage 37, and whether or not bacteria survive or propagate in the culture medium in the verification bottle 36 is verified (verifying process, step S17 in FIG. 7). As a result of this verification, if the number of the verification bottles 36 in which the bacteria survive or propagate is not more than a predetermined number (for example, zero), it is judged that the sterility in the content filling system 10 is ensured, and production of the product bottle 35 actually filled with a content such as a beverage is started. As in the case of the first embodiment, in order to shorten the period during which the culture medium in the verification bottle 36 is cultured in the constant temperature storage 37, physical movement is added to the culture medium in the verification bottle 36, and the verification bottle 36 may be stored in a state in which the culture medium is moving.

As described above, according to the present embodiment, the culture medium used for the verification is matched to the characteristics of the content to be filled actually, and the pH of the culture medium is adjusted to 4.0 or more and 4.6 or less, so that the culture medium allows survival of bacterial spores but does not allow survival of vegetative cells of bacteria, mold and yeast. Consequently, when the sterility of the content filling system 10 is comprehensively evaluated using the culture medium, verification can be performed such that the growing environment of bacteria is resembled the actual content. Thus, no excessive facilities for sterilization are necessary, and it is possible to reduce medicines and heat energy required for sterilization, so that the production cost of the product bottle 35 can be reduced. For example, it is possible to reduce the temperature of steam, hot water or the like used for Sterilizing in Place (SIP) treatment in a beverage supply system piping of the content filling system 10, or to shorten the time for flowing steam, hot water, or the like. In addition, it is possible to shorten the time required to perform Cleaning out of Place (COP) treatment or Sterilizing out of Place (SOP) treatment in the sterile chamber 70.

On the other hand, as a comparative example, when the pH of the culture medium ranges from as low acidic as 7.0 (6.0 or more and 8.0 or less) to neutral, similarly to a general culture medium, almost all the bacteria can be detected. However, when the sterility of the content filling system 10 is verified using a culture medium having a pH of 7.0 (pH 6.0 or more and 8.0 or less), in order to control the number of the verification bottles 36 in which the bacteria survive or propagate to not more than a predetermined number (for example, zero), it is required for the content filling system 10 to have a sterilizing capacity more than necessary. In this case, an excessive load may be applied to sterilization in the process of the content filling system 10, sterilization of the bottle 30 or the cap, or sterilization of the sterile chamber 70. For example, it is necessary to increase the temperature of steam, hot water and the like used for sterilization treatment, to lengthen the time for flowing steam, hot water and the like, and to increase the amount of medicine to be used. In contrast to this, in the present embodiment, since the content filled by the content filling system 10 is acidic (less than pH 4.6), there is no possibility that the content will be corrupted by bacterial spores, so that it is not required to sterilize bacterial spores in the content filling system 10. Thus, by using an acidic culture medium (having pH of 4.0 or more and 4.6 or less), it is possible to reliably verify that vegetative cells of bacteria, mold and yeast excluding bacterial spores have been killed.

(Modification)

Next, each modification of the present embodiment will be described.

In the present embodiment, the case where the characteristics of the culture medium used for verifying the content filling system 10 are the pH of the content and the pH of the culture medium is adjusted to 3.5 or more and 4.6 or less, preferably 4.0 or more and 4.6 or less has been described as an example. However, the present invention is not limited to this example.

For example, when the content to be filled by the content filling system 10 contains carbonic acid gas like carbonate drinks, the carbonic acid gas may be dissolved in the culture medium. In this case, it is preferable that the solubility of the carbonic acid gas dissolved in the culture medium is the lower limit of the solubility of carbonic acid gas dissolved in the content. In general, when the content to be filled by the content filling system 10 contains carbonic acid gas, proliferation of bacteria in the content is suppressed. Thus, by dissolving carbonic acid gas in the culture medium, sterility can be verified such that the growing environment of bacteria is resembled the actual content. Thus, it is possible to suppress facilities, medicines, energy and the like required for sterilization in the content filling system 10.

When the content to be filled by the content filling system 10 does not contain at least one of a carbon source and a nitrogen source (organic matter) like mineral water, for example, the culture medium may not contain at least one of these (or adjustment may be performed such that at least one of these is contained in an amount of 0.1% by weight or less). In general, when the content does not contain at least one of the carbon source and the nitrogen source, proliferation of bacteria propagating using at least one of the carbon source and the nitrogen source is suppressed. Thus, in accordance with this, when the culture medium does not contain at least one of the carbon source and the nitrogen source, sterility can be verified such that the growing environment of bacteria is resembled the content to be filled actually. Thus, it is possible to suppress facilities, medicines, energy and the like required for sterilization in the content filling system 10.

As the characteristics influencing propagation of bacteria, the value of the total organic carbon content (TOC=Total Organic Carbon) in the content may be used. It is also possible to verify sterility such that the value of the total organic carbon content in the culture medium is adjusted to be close to the value of the total organic carbon content of the content to be filled actually. For example, the value of TOC contained in commercially available mineral water is about 0.1 to 0.3 mg/L. Thus, when the content is mineral water, a carbon source and/or a nitrogen source is added such that the TOC value of the culture medium to be filled is, for example, 5 mg/L (preferably 0.5 mg/L), and sterility may be evaluated.

When the content to be filled by the content filling system 10 does not contain at least one of the carbon source and the nitrogen source, or is, for example, a green tea beverage containing catechin, catechin may be added to the culture medium to verify sterility. In general, when the total content of catechins in the content (the total content refers to the following eight contents: epigallocatechin (EGC), epigallocatechin gallate (EGCg), epicatechin (EC), epicatechin gallate (ECg), gallocatechin (GC), gallocatechin gallate (GCg), catechin (C), catechin gallate (Cg)) is 30 mg % or more, proliferation of bacteria is suppressed. Thus, by adding 30 mg % of the total content of catechins to the culture medium, sterility can be verified such that the growing environment of bacteria is resembled the content to be filled actually. Thus, it is possible to suppress facilities, medicines, energy and the like required for sterilization in the content filling system 10.

In the second embodiment and the modification, as culture media having characteristics (bacterial growth inhibiting factor) influencing propagation of bacteria, (i) the culture medium having a pH of 3.5 or more and 4.6 or less (preferably 4.0 or more and 4.6 or less), (ii) the culture medium with carbonic acid gas dissolved, (iii) the culture medium in which at least one of a carbon source and a nitrogen source is not contained, (iv) the culture medium with the prepared total organic carbon content, and (v) the culture medium with catechin dissolved have been described as examples. The characteristic of the culture medium is not limited to the characteristic of any one of the above (i) to (v), and a culture medium having plural characteristics among (i) to (v) may be used. For example, a culture medium in which (i) the pH is 3.5 or more and 4.6 or less and (ii) carbonic acid gas is dissolved may be used.

In the above case, although the sterilizer performing hydrogen peroxide sterilization and hot water sterilization is used as the sterilizer for the container, the present invention is not limited thereto. All sterilizers such as sterilizers using peracetic acid sterilization, electron beam sterilization, and UV sterilization can be applied. In the above example, since a PET bottle is used as the container, a culture medium for aerobic bacteria is used; however, the culture medium is not limited to this. When a retort container such as canned food is used, a culture medium for anaerobic bacteria may be used.

Examples

Next, specific examples of the present embodiment will be described.

Example 2-1

A 600 bottle per minute (bpm) beverage filling system was used in which a sterilized beverage was filled at room temperature into a 500 mL capacity PET bottle sterilized in a sterile atmosphere and the PET bottle was sealed with a sterilized cap. In this beverage filling system, containers (bottles, caps), a sterile chamber, and a product solution line were subjected to such a treatment that although bacterial spores could survive, mold, yeast and vegetative cells of bacteria could be sterilized. Then, an acidic culture medium having a pH of 4.0 was filled inside 10,000 PET bottles at room temperature by using the beverage filling system, and the PET bottles were cultured at 30° C. for 1 week. After culture, all of the PET bottles were inspected. As a result, it was confirmed that no PET bottle with a corrupted culture medium was present. After that, an acidic beverage having a pH of less than 4.0 was filled at room temperature by using the beverage filling system to produce product bottles, and then the product bottles were inspected. As a result, the acidic beverages in all the product bottles were not corrupted.

Example 2-2

A 600 bottle per minute (bpm) beverage filling system was used in which a sterilized beverage was filled at room temperature into a 500 mL capacity PET bottle sterilized in a sterile atmosphere and the PET bottle was sealed with a sterilized cap. A culture medium with carbonic acid gas dissolved was filled inside 10,000 PET bottles at room temperature by using this beverage filling system, and the PET bottles were cultured at 30° C. for 1 week. The added amount (volume) of carbonic acid gas was set to GV=2.0, which is a product lower limit gas volume. After culture, all of the PET bottles were inspected. As a result, it was confirmed that no PET bottle with a corrupted culture medium was present. After that, a carbonate drink having a gas volume of 2.0 or more was filled at room temperature by using the beverage filling system to produce product bottles, and then the product bottles were inspected. As a result, the carbonate drinks in all the product bottles were not corrupted.

Example 2-3

A 600 bottle per minute (bpm) beverage filling system was used in which a sterilized beverage was filled at room temperature into a 500 mL capacity PET bottle sterilized in a sterile atmosphere and the PET bottle was sealed with a sterilized cap. A culture medium in which the carbon source and the nitrogen source were each reduced to 0.05% by weight was filled inside 10,000 PET bottles at room temperature by using this beverage filling system, and the PET bottles were cultured at 30° C. for 3 weeks. After culture, all of the PET bottles were inspected. As a result, it was confirmed that no PET bottle with a corrupted culture medium was present. After that, mineral water was filled at room temperature to produce product bottles, and then the product bottles were inspected. As a result, the mineral water in all the product bottles was not corrupted.

Example 2-4

A 600 bottle per minute (bpm) beverage filling system was used in which a sterilized beverage was filled at room temperature into a 500 mL capacity PET bottle sterilized in a sterile atmosphere and the PET bottle was sealed with a sterilized cap. In this beverage filling system, containers (bottles, caps), a sterile chamber, and a product solution line were subjected to such a treatment that although bacterial spores could survive, mold, yeast and vegetative cells of bacteria could be sterilized. Then, a culture medium in which 30 mg % of the total content of catechins was added was filled inside 10,000 PET bottles at room temperature by using the beverage filling system, and the PET bottles were cultured at 30° C. for 1 week. After culture, all of the PET bottles were inspected. As a result, it was confirmed that no PET bottle with a corrupted culture medium was present. After that, a tea-type beverage having 30 mg % or more of the total content of catechins was filled at room temperature by using the beverage filling system to produce product bottles, and then the product bottles were inspected. As a result, the tea-type beverages in all the product bottles were not corrupted.

Example 2-5

A 600 bottle per minute (bpm) beverage filling system was used in which a sterilized beverage was filled at high temperature inside a 500 mL capacity PET bottle and the PET bottle was sealed with a cap. In this beverage filling system, an acidic culture medium having a pH of 4.0 was filled inside 10,000 PET bottles at a high temperature of 85±5° C., and the PET bottles were cultured at 30° C. for 1 week. After culture, all of the PET bottles were inspected. As a result, it was confirmed that no PET bottle with a corrupted culture medium was present. After that, an acidic beverage having a pH of less than 4.0 was filled at high temperature by using the beverage filling system to produce product bottles, and then the product bottles were inspected. As a result, the acidic beverages in all the product bottles were not corrupted.

Example 2-6

A 600 bottle per minute (bpm) beverage filling system was used in which a sterilized beverage was filled at medium temperature into a 500 mL capacity PET bottle sterilized in a sterile atmosphere and the PET bottle was sealed with a sterilized cap. In this beverage filling system, an acidic culture medium having a pH of 4.0 was filled inside 10,000 PET bottles at a medium temperature of 65±5° C., and the PET bottles were cultured at 30° C. for 1 week. After culture, all of the PET bottles were inspected. As a result, it was confirmed that no PET bottle with a corrupted culture medium was present. After that, an acidic beverage having a pH of less than 4.0 was filled at medium temperature to produce product bottles, and then the product bottles were inspected. As a result, the acidic beverages in all the product bottles were not corrupted.

The invention claimed is:

1. An initial bacteria confirmation method for confirming initial bacteria in a container with use of a content filling system having a container sterilizer which sterilizes the container, a filler which fills a content in the container, and a cap attachment device which caps the container with a cap, the method comprising:
   conveying the container to the filler without sterilizing the container by the container sterilizer;
   filling a culture medium in the container with the use of the filler;
   capping the container with the cap using the cap attachment device;
   verifying whether or not the bacteria survive or propagate in the culture medium in the container; and
   adjusting sterilization conditions in the container sterilizer based on results of the verification.

2. The initial bacteria confirmation method according to claim 1, wherein the content is acidic, and pH of the culture medium is 3.5 or more and 4.6 or less.

3. An initial bacteria confirmation method for confirming initial bacteria in a cap with use of a content filling system having a filler which fills a content in a container, a cap sterilizer which sterilizes the cap, and a cap attachment device which caps the container with the cap, the method comprising:
   of filling a culture medium in the container with the use of the filler;
   conveying the cap to the cap attachment device without sterilizing the cap by the cap sterilizer;
   capping the container with the cap using the cap attachment device; and
   verifying whether or not the bacteria survive or propagate in the culture medium in the container; and
   adjusting sterilization conditions in the cap sterilizer based on results of the verification.

4. The initial bacteria confirmation method according to claim 3, wherein the content is acidic, and pH of the culture medium is 3.5 or more and 4.6 or less.

5. An initial bacteria confirmation method for confirming initial bacteria in a container with use of a content filling system having a container sterilizer which sterilizes the container, a filler which fills a content in the container, and a cap attachment device which caps the container with a cap, the method comprising:
   conveying the container to the filler without sterilizing the container by the container sterilizer;
   filling a culture medium in the container with the use of the filler;
   capping the container with the cap using the cap attachment device; and
   verifying whether or not the bacteria survive or propagate in the culture medium in the container,
   wherein the content is neutral, and pH of the culture medium is 6 or more and 8 or less.

6. An initial bacteria confirmation method for confirming initial bacteria in a cap with use of a content filling system having a filler which fills a content in a container, a cap sterilizer which sterilizes the cap, and a cap attachment device which caps the container with the cap, the method comprising:
   filling a culture medium in the container with the use of the filler;

conveying the cap to the cap attachment device without sterilizing the cap by the cap sterilizer;

capping the container with the cap using the cap attachment device; and verifying whether or not the bacteria survive or propagate in the culture medium in the container, wherein the content is neutral, and pH of the culture medium is 6 or more and 8 or less.

7. An initial bacteria confirmation method for confirming initial bacteria in a container with use of a content filling system having a container sterilizer which sterilizes the container, a filler which fills a content in the container, and a cap attachment device which caps the container with a cap, the method comprising:

conveying the container to the filler without sterilizing the container by the container sterilizer;

filling a culture medium in the container with the use of the filler;

capping the container with the cap using the cap attachment device; and verifying whether or not the bacteria, survive or propagate in the culture medium in the container, wherein in verifying whether or not the bacteria survive or propagate, a physical movement is added to the culture medium in the container.

8. A method for verifying a content filling system using a culture medium, the method comprising:

feeding a container to the content filling system;

filling a culture medium in the container in the content filling system and then capping the container; and verifying whether or not the bacteria survive or propagate in the culture medium in the container, wherein characteristics of the culture medium are matched to characteristics of the content to be filled in the content filling system, the characteristics influencing propagation of the bacteria, and wherein the content contains carbonic acid gas, and the carbonic acid gas is dissolved in the culture medium.

9. A culture medium used for the verification method according to claim 8, wherein the characteristics of the culture medium are matched to the characteristics of the content to be filled in the content filling system, the characteristics influencing propagation of the bacteria, and carbonic acid gas is dissolved in the culture medium.

* * * * *